(12) United States Patent
Bennett et al.

(10) Patent No.: US 6,537,973 B1
(45) Date of Patent: *Mar. 25, 2003

(54) OLIGONUCLEOTIDE INHIBITION OF PROTEIN KINASE C

(75) Inventors: C. Frank Bennett, Carlsbad, CA (US); Nicholas M. Dean, Olivenhain, CA (US); Jon T. Holmlund, Carlsbad, CA (US); F. Andrew Dorr, Solana Beach, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/025,139

(22) Filed: Dec. 18, 2001

Related U.S. Application Data

(63) Continuation-in-part of application No. 08/829,637, filed on Mar. 31, 1997, now Pat. No. 6,339,066, which is a continuation-in-part of application No. 08/478,178, filed on Jun. 7, 1995, now Pat. No. 5,882,927, which is a continuation-in-part of application No. 08/089,996, filed on Jul. 9, 1993, now Pat. No. 5,703,054, which is a continuation-in-part of application No. 07/852,852, filed on Mar. 16, 1992, now abandoned.

(51) Int. Cl.$^7$ .......................... C07H 21/04; C12Q 1/68; A61K 48/00

(52) U.S. Cl. ..................... 514/44; 435/6; 435/325; 435/375; 536/24.3; 536/24.32; 536/23.1; 536/24.5

(58) Field of Search ................. 514/44; 435/6, 435/325, 375; 536/24.3, 24.5, 24.32, 23.1

(56) References Cited

U.S. PATENT DOCUMENTS

| | | | | |
|---|---|---|---|---|
| 3,336,289 | A | 8/1967 | Wechter et al. | 536/26.7 |
| 3,687,808 | A | 8/1972 | Merrigan et al. | 536/24.5 |
| 3,792,039 | A | 2/1974 | Erickson et al. | 536/25.5 |
| 3,846,402 | A | 11/1974 | Eckstein et al. | 536/26.23 |
| 4,310,662 | A | 1/1982 | Crea | 536/25.31 |
| 4,381,344 | A | 4/1983 | Rideout et al. | 435/320.1 |
| 4,500,707 | A | 2/1985 | Caruthers et al. | 536/25.34 |
| 4,511,713 | A | 4/1985 | Miller et al. | 435/6 |
| 4,591,614 | A | 5/1986 | Miller et al. | 536/24.5 |
| 4,663,446 | A | 5/1987 | Wright | 536/26.26 |
| 4,689,320 | A | 8/1987 | Kaji | 514/44 |
| 4,760,017 | A | 7/1988 | McCormick | 435/6 |
| 4,806,463 | A | 2/1989 | Goodchild et al. | 435/5 |
| 4,835,263 | A | 5/1989 | Nguyen et al. | 536/27 |
| 4,876,335 | A | 10/1989 | Yamane et al. | 536/24.3 |
| 4,965,350 | A | 10/1990 | Inoue et al. | 536/22.1 |
| 5,004,810 | A | 4/1991 | Draper | 536/27 |
| 5,011,909 | A | 4/1991 | Borovsky et al. | 530/328 |
| 5,034,506 | A | 7/1991 | Summerton et al. | 528/391 |
| 5,087,617 | A | 2/1992 | Smith | 514/44 |
| 5,098,890 | A | 3/1992 | Gewirtz et al. | 514/44 |
| 5,130,253 | A | 7/1992 | Borovsky et al. | 435/320.1 |
| 5,135,917 | A | 8/1992 | Burch | 514/44 |
| 5,138,045 | A | 8/1992 | Cook et al. | 536/27 |
| 5,166,195 | A | 11/1992 | Ecker | 514/44 |
| 5,194,428 | A | 3/1993 | Agrawal et al. | 514/44 |
| 5,212,295 | A | 5/1993 | Cook | 536/26.7 |
| 5,218,105 | A | 6/1993 | Cook et al. | 536/25.31 |
| 5,242,906 | A | 9/1993 | Pagano et al. | 514/44 |
| 5,248,670 | A | 9/1993 | Draper et al. | 514/44 |
| 5,264,423 | A | 11/1993 | Cohen et al. | 514/44 |
| 5,276,019 | A | 1/1994 | Cohen et al. | 514/44 |
| 5,286,717 | A | 2/1994 | Cohen et al. | 514/44 |
| 5,378,825 | A | 1/1995 | Cook et al. | 536/25.34 |
| 5,386,023 | A | 1/1995 | Sanghvi et al. | 536/25.3 |
| 5,457,191 | A | 10/1995 | Cook et al. | 536/27.13 |
| 5,459,255 | A | 10/1995 | Cook et al. | 536/27.13 |
| 5,506,212 | A | 4/1996 | Hoke et al. | 514/44 |
| 5,512,438 | A | 4/1996 | Ecker | 435/6 |
| 5,521,302 | A | 5/1996 | Cook et al. | 536/25.31 |
| 5,539,082 | A | 7/1996 | Nielsen et al. | 530/300 |
| 5,541,307 | A | 7/1996 | Cook et al. | 536/23.1 |
| 5,554,746 | A | 9/1996 | Ravikumar et al. | 540/200 |
| 5,571,902 | A | 11/1996 | Ravikumar et al. | 536/22.1 |
| 5,578,718 | A | 11/1996 | Cook et al. | 536/27.21 |
| 5,587,361 | A | 12/1996 | Cook et al. | 514/44 |
| 5,620,963 | A | 4/1997 | Cook et al. | 514/44 |
| 5,703,054 | A | * 12/1997 | Bennett et al. | 435/194 |
| 5,821,072 | A | * 10/1998 | Schwartz et al. | 424/9.2 |
| 5,882,927 | A | 3/1999 | Bennett et al. | 435/375 |

FOREIGN PATENT DOCUMENTS

| EP | 0506242 | 9/1992 |
|---|---|---|
| JP | 7011506 | 4/1970 |
| JP | 7307354 | 3/1973 |
| WO | WO 89/03683 | 5/1989 |
| WO | WO 91/08313 | 6/1991 |
| WO | WO 92/20823 | 11/1992 |
| WO | WO 93/20101 | 10/1993 |
| WO | WO 94/29455 | 12/1994 |
| WO | WO 96/32496 | 10/1996 |
| WO | WO 96/34008 | 10/1996 |

OTHER PUBLICATIONS

Ahamad, et al., "Antisense Expression of Protein Kinase Cα Inhibits the Growth and Tumorigenicity of Human Glioblastoma Cells", *Neurosurg.*, 1994, 35, 904–909.

(List continued on next page.)

*Primary Examiner*—Andrew Wang
*Assistant Examiner*—James Douglas Schultz
(74) *Attorney, Agent, or Firm*—Woodcock Washburn LLP

(57) ABSTRACT

Compositions and methods are provided for the treatment and diagnosis of diseases associated with protein kinase C. Oligonucleotides are provided which are targeted to nucleic acids encoding PKC. In preferred embodiments, the oligonucleotides contain one or more chemical modifications. Methods of modulating PKC expression and of treating animals suffering from disease amenable to therapeutic intervention by modulating protein kinase C expression using oligonucleotides targeted to PKC are disclosed.

18 Claims, 16 Drawing Sheets

OTHER PUBLICATIONS

Alberts, et al., "Molecular Biology of the Cell", pp. 411–415, Garland Publishing, Inc., New York, 1983.

Bacher, et al., "Isolation and Characterization of PKC–L, A New member of the Protein Kinase C–Related Gene Family Specifically Expressed in Lung, Skin, and Heart", *Mol. Cell. Biol.*, 1991, 11, 126–133.

Ballester, et al., "Fate of Immunoprecipitable Protein Kinase C in $GH_3$ Cells Treated with Phorbol 12–Myristate 13–Acetate", *Biol. Chem.*, 1985, 260, 15194–15199.

Borek, et al., "Long–chain (sphingoid) bases inhibit multistage carcinogenesis in mouse C3H/10T1/2 cells treated with radiation and phorbol 12–myristate 13–acetate", *Proc. Natl. Acad. Sci. USA*, 1991, 88, 1953–1957.

Brigstock, et al., "Species–Specific High Molecular Weight Forms of Basic Fibroblast Growth Factor", 1990, 4, 45–52.

Brody and Frey, "Unambiguous determination of the sterochemistry of nucleotidyl transfer catalyzed by DNA polymerase I from *Escherichia coli*", *Biochemistry*, 1981, 20, 1245–1252.

Brody and Frey, "Stereochemical course of nucleotidyl catalyzed by bacteriophage T7 induced DNA polymerase", *Biochemistry*, 1982, 21, 2570–2572.

Burgers and Eckstein, "A Study of the mechanism of DNA polymerase I from *Escherichia coli* with diastereomeric phosphorothioate analogs of deoxyadenosine triphosphate", *J. Biol. Chem.*, 1979, 254, 6889–6893.

Burgers and Eckstein, "Absolute configuration of the diastereomers of adenosine 5'–O–(1–thiotriphosphate): Consequences for the stereochemistry of polymerization by DNA–dependent RNA polymerase from *Escherichia coli*", *Proc. Natl. Acad. Sci. USA*, 1978, 75, 4798–4800.

Coussens, et al., "Multiple, Distinct Forms of Bovine and Human Protein Kinase C Suggest Diversity in Cellular Signaling Pathways", *Science*, 1986, 233, 859–866.

Crokke, et al., "Pharmacokinetic Properties of Several Novel Oligonucleotide Analogs in mice", *J. Pharmacol. Exp. Ther.*, 1996, 277, 923–937.

Cruse, et al., "Chiral Phosphorothioate Analogues of B–DNA", *J. Mol. Biol.*, 1986, 192, 891–905.

Dagle, et al., "Targeted degradation of mRNA in Xenopus oocytes and embryos directed by modified oligonucleotides: studies of An2 and cyclin in embryogenesis", *Nucleic Acids Research*, 1990, 18, 4751–4757.

Dagle, et al., "Pathways of Degradation and Mechanism of Action of Antisense Oligonucleotides in *Xenopus laevis* Embryos", *Antisense Research and Development*, 1991, 1, 11–20.

Dagle, et al., "Physical properties of oligonucleotides containing phosphoramidate–modified internucleoside linkages", *Nucleic Acids Research*, 1991, 19, 1805–1810.

DeVirgilio, et al., "Cloning and Disruption of a Gene Required for Growth on Acetate but not on Ethanol: The Acetyl–Coenzyme A Synthetase Gene of *Saccharomyces cerevisiae*", *Yeast*, 1992, 8, 1043–1051.

Eckstein and Jovin, "Assignment of Resonances in the Phosphorus–31 Nuclear Magnetic Resonance Spectrum of Poly[d(A–T)] from Phosphorothioate Substitution", *Biochemistry*, 1983, 2, 4546–4550.

Eder, P.S. and Walder, J.A., "Ribonuclease H from K562 Human Erythroleukemia Cells", *J. Biol. Chem.*, 1991, 266, 6472–6479.

Endo, et al., "Cell Membrane Signaling as Target in Cancer Therapy: Inhibitory Effect of N,N–Dimethyl and N,N,N–Trimethyl Sphingosine Derivatives on In Vitro and In Vitro Growth of Human Tumor Cells in Nude Mice", *Cancer Research*, 1991, 51, 1613–1618.

Ettinger, L., et al., "Intrathecal Methotrexate Overdose Without Neurotoxicity", *Cancer*, 1978, 41, 1270–1273.

French, et al., "Expression of Two Related Nonstuctural Proteins of bluetongue Virus (BTV) Type 10 in Insect Cells by a Recombinantbaculovirus: Production of Polyclonal Ascitic Fluid and Characterization of the Gene Product in BTV–Infected BHK Cells", *J. Virol.*, 1989, 63, 3270–3278.

Gao, et al., "Cloning and Characterization of Mouse Gene with Homology to the Human von Hippel–Lindau Disease Tumor Suppressor Gene: Implications for the Potential Organization of the Human von Hippel–Lindau Disease Gene", *Cancer Res.*, 1995, 55, 743–747.

Gebeyehu, G., et al., "Novel biotinylated nucleotide—analogs for labeling and colorimetric detection of DNA", *Nucleic Acid Res.*, 1987, 15, 4513–4534.

Gelbert, et al., "Analysis of GPT Activity in Mammalina Cells with a Chromosomally Integrated Shuttle Vector Containing Altered gpt Genes", *Somat. Cell. Mol. Genet.*, 1990, 16, 173–184.

Gescher, et al., "Protein Kinase C–A Novel Target for Rational Anti–Cancer Drug Design", *Anti–Cancer Drug Design*, 1989, 4, 93–105.

Godson, et al., "Inhibition of Expression of Protein Kinase C α by Antisense cDNA Inhibits Phorbol Ester–Mediated Archidonate Release", *J. Biol. Chem.*, 1993, 268, 11946–11950.

Gold and Stormo in: "Translational Initiation", Department of Molecular, Cellular and Developmental Biol., 1987, vol. 2, Chapter 78, pp. 1302–1307.

Greenberg, M.E. in Current Protocols in Molecular Biology, F.M., Ausubel, et al., Eds., John Wiley & Sons, NY 1987.

Gupta, et al., "Template–Primer–dependent Turnover of (Sp)–dATPαS by T4 DNA Polymerase", *J. Biol. Chem.*, 1982, 257, 7689–7692.

Hegemann, L. And G. Mahrle, "Pharmacology of the Skin", H. Mukhtar, ed., pp. 357–368, CRC Press, Boca Raton, FL, 1992.

Henthorn, P., et al., "Expression of a human placental alkaline phosphatase gene in transfected cells: use as a reporter for studies of gene expression", *Proc. Natl. Acad. Sci. USA*, 1988, 85, 6342–6346.

Hidaka and Hagiwara, "Pharmacology of the isoquinoline sulfonamide protein kinase C inhibitors", *Trends in Pharm. Sci.*, 1987, 8, 162–164.

Kabanov, et al., "A new class of antivirals: antisense oligonucleotides combined with a hydrophobic substituent effectivey inhibit influenza virus reproduction and synthesis of virus–specific proteins in MDCK cells", *FEBS Lett.*, 1990, 259, 327–330.

Kanagasundaram, V. And Scopes, R., "Isolation and characterization of a gene encoding gluconolactonase from *Zumomonas mobilis*", *Biochim. et Biophys. Acta*, 1992, 1171, 198–200.

Kornberg, A., DNA Replication, pp. 75–77, W.H. Freeman & Co., San Francisco, 1980.

Krug, et al., "Evidence for increased synthesis as well as increased degradation of protein kinase C after treatment of human ostersarcoma cells with phorbol ester", *J. Biol. Chem.*, 1987, 262, 11852–11856.

Kubo, et al., "Primary strucures of human protein kinase CBI and BII differ only in their C–terminal sequences", *FEBS Lett.*, 1987, 223(1), 138–142.

Letsinger, et al., "Cholesteryl–conjugated oligonucleotides: Synthesis, properties and activity as inhibitors of replication of human immunodeficiency virus in cell culture", *Proc. Natl. Acad. Sci. USA*, 1989, 86, 6553–6556.

Ludwig and Eckstein, "Rapid and efficient synthesis of nucleoside 5'–O–(1–thiotriphosphates), 5'–triphosphates and 2' ,3'–cyclophosphorothioates using 2–chloro–4H–1,3, 2–benzodioxaphosphorin–4–one", *J. Org. Chem.*, 1989, 54, 631–635.

Luer and Hatton, "Vancomycin Administration into the Cerebrospinal Fluid: A Review", *The Annals of Pharmacotherapy*, 1993, 27, 912–921.

Manoharan, et al., "Introduction of a Lipophilic Thioether Tether in the Minor Groove of Nucleic Acids for Antisense Applications", *Bioorg. Med. Chem. Lett.*, 1993, 3, 2765–2770.

Manoharan, et al., "Chemical Modifications to Improve Uptake and Bioavailability of Antisense Oligonucleotides", *Ann. N.Y. Acad. Sci.*, 1992, 660, 306–309.

Manoharan, et al., "Cholic Acid–Oligonucleotide Conjugates for Antisense Applications", *Bioorg. Med. Chem. Lett.*, 1994, 4, 1053–1060.

Manoharan, et al., "Lipid Nucleic Acids", *Tetrahedron Lett.*, 1995, 36, 3651–3654.

Manoharan, et al., "Oligonucleotide Conjugates: Alteration of the Pharmacokinetic Properties of Antisense Agents", *Nucleosides & Nucleotides*, 1995, 14, 969–973.

Markussen, et al., "Translational control of oskar generates Short OSK, the isoform that induces poly plasm assembly", *Development*, 1995, 121, 3723–3732.

Martin, et al., "Ein neuer Zagang zu 2'–O–Alkylribonucleosiden und Eigenschaften deren Oligonucleotide", *Helv. Chim. Acta.*, 1995, 78, 486–504.

The Merck Manual of Diagnosis and Therapy, 15th Ed., pp. 1206–1228, Berkow, et al., eds., 1987, Rahya, N.J., 1987.

McDermott, et al., "Structural and lens expression of the gene encoding chicken βA3/A1–crystallin", *Gene*, 1992, 117, 193–200.

Minsull and Hunt, "The use of single–stranded DNA and RNase H to promote quantitative 'hybrid arrest of translations' of mRNA/DNA hybrids in reticulocyte lysate cell–free translation", *Nucl. Acid Res.*, 1986, 14, 6433–6451.

Mishra, et al., "Improved leishmanicidal effect of phosphorothiate antisense oligonucleotide by LDL–mediated delivery", *Biochim. Biophys. Acta*, 1995, 1264, 229–237.

Monaco, et al., "Structure of Two Rat Genes Coding for Closely Related Rolipram–sensitive cAMP Phosphodiesterases", *J. Biol. Chem.*, 1995, 269, 347–357.

Nielsen, et al., "Sequence–Selective Recognition of DNA by Strand Dsiplacement with a Thymine–Substituted Polyamide", *Science*, 1991, 254, 1497–1500.

Nishizuka, et al., "The Molecular Heterogeneity of Protein Kinase C and its Implications for Cellular Regulation", *Nature*, 1988, 334, 661–665.

Oberhauser, et al., "Effective incorporation of 2'–O–methyl–oligoribonucleotides into liposomes and enhanced cell association through modification with thiocholesterol", *Nucl. Acids Res.*, 1992, 20, 533–538.

Olsen, et al., "Inhibition of Protein Kinase–A by Overexpression of the Cloned Human Protein Kinase Inhibitor", *Mol. Endocrinol.*, 1991, 5, 1246–1256.

Osada, et al., "A phorbol ester receptor–protein kinase, nPKCη, a new member of the protein kinase C family predomintly expressed in lung and skin", *J. Biol. Chem.*, 1990, 265, 22434–22440.

Parker, et al., "The complete primary structure of potein kinase c–the major phorbol ester receptor", *Science*, 1986, 233, 853–866.

Perri, et al., "Interactions of Plasmid–encoded Replication Initiation Proteins with the Origin of DNA Replication in the Broad Host Range Plasmid RK2", *J. Biol. Chem.*, 1991, 266, 12536–12543.

Pushpa–Rekha, et al., "Rat Phospholipid–hydroperoxide Glutathione Peroxidase", *J. Biol. Chem.*, 1995, 270, 26993–26999.

Rogers, et al., "Alternative splicing dictates translational start in Epstein–Barr virus transcripts", *EMBO J.*, 1990, 9, 2273–2277.

Romaniuk and Eckstein, "A study of the mechanism of t4 DNA polymerase with diasteromeric phosphorothioate analogues of deoxyadenosine triphosphate", *1982, J. Biol. Chem.*, 257(13), 7684–7688.

Saison, Behmoaras, et al., "Short modified antisense oligonucleotides directed against Ha–ras point mutation induce selective cleavage of the mRNA and inhibit T24 cells proliferation", *EMBO J.*, 1991, 10, 1111–1118.

Sambrook, et al., Molecular Cloning. A Laboratory Manual., vol. 2, Cold Spring Harbor Laboratory Press, Cold Spring Harbor, N.Y., p. 10.59, 1989.

Saul, et al., "celB, a Gene Coding for a Bifunctional Cellulase from the Extreme Thermophile *Caldocellum saccharolyticum*", *Appl. Environ. Microbiol.*, 1990, 56, 3117–3124.

Shea, et al., "Synthesis, hybridization properties and antiviral activity of lipid–oligodeoxynucleotide conjugates", *Nucl. Acids Res.*, 1990, 18, 3777–3783.

Stec, J.W., Oligonucletotides as Antisense Inhibitors of Gene Expression: Therapeutic Implications, Meeting Astracts, Jun. 18–21, 1989.

Stec, et al., "Novel Route to Oligo(Deoxyribonucleoside Phosphorothiates). Sterocontrolled Synthesis of P–chiral Oligo(Deoxyribonucleoside Phosphorothiates)", Nucleic Acids Res., 1991, 19, 5883–5888.

Stec and Lesnikowski, "Stereospecific Synthesis of P–Chiral Analogs of Oligonucleotides", in "Methods in Molecular Biology", S. Agrawal, Ed., 1993, 20, 285–313.

Stec, et al., "Reversed–phase High–performance Liquid Chromatographic Separation of diastereomeric Phosphorothioate Analogues of Oligodeoxyribonucleotides and Other Backbone–Modified Congerers of DNA" *Chromatography*, 1985, 326, 263–280.

Svinarchuk, et al., "Inhibition of HIV proliferation in MT–4 cells by antisense oligonucleotide conjugated to lipophilic groups", *Biochimie*, 1993, 75, 49–54.

Ueda, et al., "Phosphorothioate–containing RNAs show mRNA activity in the prokaryotic translation systems in vitro", *Nucl. Acids Research*, 1991, 19, 547–552.

Weinstein, I.B., "Cancer Prevention: Recent Progress and Future Opportunities", Cancer Res. Suppl., 1991, 51, 5080s–5085s.

Yaoita, et al., "*Xenopus laevis* α and β thyroid hormone receptors", *Proc. Natl. Acad. Sci. USA*, 1990, 87, 7090–7094.

Young, S., et al., "Down-regulation of protein kinase C is due to an increased rate of degradation", *Biochem. J.,* 1987, 244, 776–779.

Zimm, S., et al., "Cerebrospinal Fluid Pharmacokinetics of Intraventricular and Intravenous Aziridinylbenzoquinone", *Cancer Research,* 1984, 44, 1698–1701.

Bryant, F. and Benkovic, S., "Stereochemical course of the reaction catalyzed by 5'–nucleotide phosphodiesterase from snake venom", *Biochemistry,* 1979, 2825–2628.

Eckstein, F. And Jovin, T.M., "Nucleoside Phosphorothioates", *J. Am. Chem. Soc.,* 1966, 88, 4292.

Eckstein, F., "Nucleoside Phosphorothioates", *J. Am. Chem. Soc.,* 1970, 92, 4718–4723.

Doerr and Fox, "Nucleosides. XL. The Introduction of a 2,3'–Imino Bridge into Pyrimidine Nucleosides", *J. Am. Chem.,* 1967, 89, 1760–1761.

Haga, K., et al., "The preparation of halo–nucleosides", *Bull. Of the Chem. Soc. Jpn.,* 1970, 43, 3922–3924.

Fuji, et al., "Acylphosphonates. 7.[1] A New Method for Stereospecific and Stereoselective Generation of Dideoxyribonucleoside Phosphorothioates via the Acylphospone Intermediates", *Tetrahedron,* 1987, 43, 3395–3407.

Gupta, et al., "Template–Primer–Dependent Turnover of (Sp)–dATP S by T4 DNA Polymeraes", *J. Bio. Chem.,* 1982, 247, 7689–7692.

Goodchild, "Conjugates of Oligonucleotides and Modified Oligonucleotides: A Review of Their Synthesis and Properties", *Bioconjugate Chem.,* 1990, 1, 166–187.

Koole, L.H., et al., "Enhanced stability of a Watson & Crick DNA duplex structure by methylation of the phosphate groups in one strand", *Proc. K. Ned. Acad. Wet.,* 1987, 90(1), 41–46.

Jager, A., et al., "Oligonucleotide N–alkylphosphoramidates: Synthesis and binding to polynucleotides", *Biochemistry,* 1988, 27, 7237–7246.

Holy, A. And Storm, F., "Oligonucleotidic compounds. XXXII. Phosphorylation of 1–lyxofuranosyl, 1–xylofuranosyl and 1–arabinofuranosyl derivatives of uracil and thymine with thriethyl hosphite and hexachloroacetone", *Collection Czechoslov., Chem. Commun.,* 1969, 34, 1929–1953.

Holy A., "Nucleic acid components and their analogues. IC. synthesis of 6–azauridine 5'–methanephosponate and 6–azauridine 2'(3')–methanephosphonate", *Collection Czechoslov. Chem. Commun.,* 1967, 32, 3713–3718.

Lee, W.W., et al., "Xylo–and Arabinofuranosylthioguanine and Related Nucleosides Derived from 2–Acetamido–6–chloropurine", *J. Of Medicinal Chem.,* 1971, 14, 820–823.

Ikehara, et al., "Purine Cyclonucleosides–8 Selective Sulfonylation of 8–Bromoadenosine Derivatives and an Alternate Synthesis of 8,2'–and 8,3'–S–Cyclonucleosides", *Tetrahedron,* 1970, 26, 4251–4259.

Kondo, K., et al., "Studies on biologically active nucleosides and nucleotides.3. synthesis of 9–(3–bromo–3–deoxy–2, 5–di–O–acetyl–B–D–xylofuranosyl) adenine", *J. Org. Chem.,* 1977, 42(24), 3967–3968.

Goodman, L. And Hubert–Habart, M., "The Direct Formation of a 3', 5'–Cyclic Mononucleotide from an Adenine Nucleoside", *Chem. Commun.,* 1969, 740–741.

Letters, R., et al., "$O^2$, 3'–Cyclouridine", *J. Chem. Soc.,* 1961, 1410–1413.

Lichtenthaler, F.W., et al., Chem. Ber., 1969, 102, 964.

Niewiarowski, W., et al., "Diastereomers of Thymidine 3'O–(Methanephosphono–thioate): Synthesis, Absolute Configuration and Reaction with 3'–methoxyacetylthymidine Under Conditions of Triester Approach to Oligonucleotide Synthesis", *Acta Bioichimica Polonica,* 1987, 34:217–231.

Scheit, Karl Heinz, "Nucleotides with Modified Phosphate Groups, in Nucleotide Analogs" John Wiley & Sons, 1980, Chapter Four and Chapter Six.

Suzaki, et al., "Synthesis of 9–β–D–Xylofuranosyl–6–mercaptopurine and 9–β–D–Xylofuranosylfuanine 5'–Phosphate", *Chem. Pharm. Bull.,* 1970, 18, 172–176.

Marmuto, R., et al., "One–Step Halogenation at the 2'–Position of Uridine, and Related Reactions of Cytidine and N'–Acetylcytidine", *Pharm. Bull.,* 1974, 22, 128–134.

Mizuno, Y., et al., "Syntheses of Potential Antimetabolites. XV. Syntheses of a Sulfonate Analog of Adenosine 5'–Phosphate and an Alternative Synthesis of 5',8–S–Anhydroadenine Nucleosides and 5'–Deoxyspongoadenosine and Its Isomers", *J. Org. Chem.,* 1974, 39, 1440–1444.

Reese, "The Chemical Synthesis of Oligo– and Polynucleotides by the Phosphotriester Approach", *Tetrahedron,* 1978, 34, 3143–3179.

Robins, et al., "Nucleic acid related compounds. 11. adenosine 2',3'–ribo–epoxide. synthesis, intromolecular degradation, and transformation into 3'–substituted xylofuranosyl nucleosides and the lyxo–epoxide[1,2]", *J. Org. Chem.,* 1974, 39(11), 1564–1570.

Miller, P.S., et al., "Biochemical and Biological Effects of Nonionic Nucleic Acid Methylphosphonates", *Biochemistry,* 1981, 20, 1874–1880.

Uhlmann, E. And Peyman, A., "Antisense oligonucleoties: A new therapeutic principle", *Chemical Reviews,* 1990, 90(4), 578–584.

Murray, A.W., et al., "Adenosine 5'–Phosphorothioate. A Nucleotide Analog that is a Sustrate, Competitive Inhibitor, or Regulator of Some Enzymes That Interact with Adenosine 5'–Phosphate", *Biochemistry,* 1968, 4023–4029.

Mizuno, Y., et al., "A Novel Synthesis of Purine β–D–Nucleosides via Purine 8,5'–S–Anhydronucleosides", *J. Am. Chem. Soc.,* 1972, 94, 4737–4739.

Miller, N., et al., "Nucleosides. XXI. Synthesis of Some 3'–Substituted 2',3'–Dideoxyribonucleosides of Thymine and 5–Methylcytosine", *J. Org. Chem.,* 1964, 29, 1772–1776.

Szarek, et al., "Synthesis of 5–Deoxy–D–xylo–Hexose and 5–Deoxy–L–arabino–Hexose, and Their Conversion into Adenine Nucleosides", *Carbohydrate Res.,* 1978, 62, 89–103.

Schuman, D., et al., *J. Am. Chem. Soc.,* 1970, 92, 3434.

Reist, et al., "Synthesis of 9–(5–Deoxy–B–D–arabinofuranosyl) adenine", *J. Org. Chem.,* 1965, 30, 3401–3403.

Wiberg, "Physical Organic Chemistry", John Wiley & Sons, New York, 1964, p. 424.

Letsinger, et al., "Effects of pendant groups at phosphorus on binding properties of d–ApA analogues", *Nucleic Acids Res.,* 1986, 14, 3487–3499.

Wempen, I. And Fox, "Nucleosides. LV. Synthesis of a sulfur–bridged thymine anhydro nucleoside and derivatives", *J. Org. Chem.,* 1969, 34, 1020–1025.

Wijen, M.H., "Disproportionation and Recombination Reactions of Methyl and n–Pentyl Radicals", *J. Am. Chem. Soc.,* 1961, 83, 3752–3754.

Cohen, J., "Oligonucleotides Inhibitors of Gene Expression", CRC Press, Boca Raton, FL, 1989, pp. 7–116, 137–210.

Guga, P. And Okruszek, A., "Stereospecific conversion of p–chiral nucleoside phosphorothioates", *Tetrahedron Letters*, 1984, 25, 2897–2900.

Jarvest, R.L. and Lowe, G., "Synthesis of methyl (R) and (S)–[$^{18}$O]phosphorothioates and determination of the absolute configuration at phosphorus of the diasteroisomers of adenosine 5'–(1–thiotriphosphate)", *J.C.S. Chem. Comm.*, 1979, 364–366.

Lee, Choongeun and Suhadolnik, Robert J., "2',5'–Oligoadenylates Chiral at Phosphorus: Enzymatic Synthesis, Properties, and Biological Activities of 2',5'–Phosphorothioate Trimer and Tetramer Analogues Synthesized from (Sp)–ATPαS", *Biochemistry*, 1985, 24(3), 551–555.

Lesnikowski, et al., "Octa(thymidine methanephosphonates) of partially defined stereochemistry: synthesis and effect of chirality at phosphorous on binding to pentadecadeoxyriboadenylic acid", *Nucleic Acids Res.*, 1990, 18(8), 2109–2115.

Richard, J.P. and Frey, P.A., "Stereochemical course of phosphoanhydride synthesis", *J. Am. Chem. Soc.*, 1983, 105, 6605–6609.

Sammons, R. Douglas and Frey, Perry A., "Synthesis of $R_P$ and $S_P[\alpha-^{18}O]$ADP from $S_P$ and $R_P$ β–Cyanoethyl–Adenosine 5'–[1–Thiodiphosphate]", *J. Biol. Chem.*, 1982, 257(3), 1138–1141.

Sopchik, et al., "$^{17}$O NMR of diastereomeric 3',5'–Cyclic Thymidine Methyl hosphates, Methylphosphonates, and N,N–Dimethyl phosphoramidates. Phosphorus Configuration of P–Chiral [$^{17}$O, $^{18}$O]–Nucleoside Phosphate Diesters", *Tetrahedron Letters*, 1989, 30(10), 1221–1224.

Stec, et al., "Synthesis and Absolute Configuration of P–Chiral O–Isopropyl Oligonucleotide Triesters", *Tetrahedron Letters*, 1985, 26(18), 2191–2194.

Stec, et al., "Solid–Phase Synthesis, Separation, and Stereochemical Aspects of P–Chiral Methane–and 4,4'–Dimethoxytriphenylmethanephosphonate Analogs of Oligodeoxyribonucleotides", *J. Org. Chem.*, 1985, 50(20), 3908–3913.

Van Pelt, Jean E., et al., "Gentamicin Nucleotidyltransferase; Stereochemical Inversion at Phosphorus in Enzymatic 2'–Deoxyadenyl Transfer to Tobramycin", *J. Biol. Chem.*, 1986, 261(34), 15995–15999.

Tsai, M.D., "Stereochemistry of the hydrolysis of adenosine 5'–thiophosphate catalyzed by venom 5'–nucleotidase", *Biochemistry*, 1980, 19, 5310–5316.

Ludwig, J. And Eckstein, F., "Rapid and efficient synthesis of nucleoside 5'–O–(1–thiotriphosphates), 5'–triphosphates and 2',3'–cyclophosphorohioates using 2–chloro–4H–1,3, 2–benzodioxzphosphorin–4–one", *J. Org. Chem.*, 1989, 54, 631–635.

Rothenberg, et al., "Oligodeoxynucleotides as anti–sense inhibitors of gene expression: therapeutic implication", *National Cancer Institute*, 1989, 81(20), 1539–1565.

Agrawal, S., et al., "Oligodeoxynucleoside Phosphoramidates and Phosphorothioates as Inhibitors of Human Immunodeficiency Virus", *PNAS USA*, 1988, 85, 7079–7083.

Marcus–Sekura, C.J., et al., "Comparative inhibition of chloramphenicol acetyltrasferase gene expression by antisense oligonucleotide analogues having alkyl phosphotriester, methylphosphonate and phosphorothioate linkates", *Nucleic Acids Research*, 1987, 15, 5749–5763.

Follman, H. And Hogenkamp, "Interaction of Ribonucleotide Reductase with Ribonucleotide Analogs", *Biochemistry*, 1971, 10, 186–187.

Seela, F., et al., "Phosphoramidites of (oxygen–18) Chiral (Rp)–and (Sp)–configurated Dimer–blocks and their use in Automated Oligonucleotide Synthesis", *Nucleosides and Nucleotides*, 1987, 6(1–2), 451–456.

Borovsky, D., "Isolation and Characterization of Highly Purified Mosquito Oostatic Hormone", *Archives of Insect Biochem. And Physiol.*, 1985, 2, 333–349.

Borovsky, D., "Oostatic Hormone Inhibits Biosynthesis of Midgut Proteplytic Enzymes and Egg Development in Mosquitoes", *Archives of Insect Biochemistry and Physiol.*, 1988, 7, 187–210.

Borovsky, D., "Mosquito oostatic factor: a novel decapeptide modulating trypsin–like enzyme biosynthesis in the midgut", *FASEB*, 1990, 4, 3015–3020.

Borovsky, D., et al., "Development of Specific RIA and ELISA to Study Trypsin Modulating Oostatic Factor in Mosquitoes", *Archives of Insect Biochem. and Physiol.*, 1992, 21, 13–21.

Rayne, R.C., and O'Shea, M., "Inactivation of Neuropeptide Hormones (AKH 1 and AAKH II) Studies In Vivo and In Vitro", *Instect Biochem. Molec. Biol.*, 1992, 22(1), 25–34.

Charbonneau, Harry "Strategies for Obtaining Partial Amino Acid Sequence Data from Small Quantities (>5nmol) of Pure of Partially Purified Protein", A Practical Guide to Protein and peptide purification for Microsequencing, pp. 15–30.

Sober, H.A., (1968), "Handbook of Biochemistry", The Chemical Rubber Co., Cleveland, Ohio, p. C70.

Baxter, et al., "PKC–episilon is involved in granulocyte–macrophage colong–stimulating facto signal transduction: Evidence from microphysiometry and antisense oligonucleotide experiments", *Biochemistry*, 1992, 31, 10950–10954.

Brandt, et al., "District Patterns of Expression of Different Protein Kinase CmRNA's in Rat Tissues", *Cell.*, 1987, 49, 57–63.

Farese, et al., "Antisense DNA downregulates protein kinase C isozymes (beat and alpha) and insulin–stimulated 2–deoxyglucose uptake in rat adipocytes", *Antisense Res. Dev.*, 1(1), 1991, 35–42.

Finkenzeller, G., "Sequence of Human Protein Kinase C α", *Nucleic Acids Research*, 1990, 18, 2183.

Hackh's Chemical Dictionary, Grant, et al. (Ed.), McGraw–Hill Book Company, New York, p. 312.

Maister, Bioworld Today, Apr. 29, 1994, p. 3.

Standaert, et al., 1991, Cellular Biochem. (Keystone Symposia on Molecular and Cellular Biology, 18–25 (Jan.), Suppl. 15B, p. 26, abstract CA 211.

Maier, et al., "An oligomer targeted against protein kinase C alpha prevents interleukin–1 alpha indiction of cycloxygenase expression in humna endothelial cells", *Exp. Cell. Res.*, 1993, 205(1), 52–58.

Marcus–Sekura, "Techniques for Using Antisense Oligodeoxyribonucleotides to Study Gene Expression", *Analytical Biochemistry*, 1988, 172, 289–295.

Sakanou, Youichirou, et al., "Protein Kinase C Activity as Marker for Colorectal Cancer", *Int. J. Cancer*, 1991, 48, 803–806.

Simons, et al., "Antisense c–myb oligonucleotides inhibit intimal arterial smooth muscle cell accumulation in vivo", 1992, 359, 67–70.

1993 Catalog of Products for DNA Research, Glen Research, Sterling, VA, p. 21.

Watson, et al, 1987, in Molecular Biology of the Gene, fourth edition, Benjamin/Cummings Publishing Company, Menlo Park, CA, p. 241.

Webster's II New Riverside University Dictionary, Soukkhanov, et al., (eds.) 1984, Houghton Mifflin Company, Boston, MA, p. 68.

Zon, "Oligonucleotide analogues as Potential Chemotherapeutic Agents", *Pharmaceuticals Res.*, 1988, 5, 539–549.

Ono, et al., "The structure, expression and properties of additional members of the protein kinase C family", *J. Biol. Chem.*, 1988, 263(14), 6927–6932.

Kawasaki, et al., "Synthesis and Biophysical Studies of 2'–dRIBO–2'–F Modified Oligonucleotides", Conference on Nucleic Acid Therapeutics, Clearwater, FL, Jan., 1991.

Daluge and Vince, "Synthesis annd Antimicrobial Activity of a Carbocyclic Puromycin Analog.6–Dimethyamino–9–{R–2Rhydroxy–3R–(p–methoxyphenyl–L–alanylamino]–cyclopentyl}purine", *Journal of Medicinal Chem.*, 1971, 15, 171–177.

Ikehara, et al., "Recognition by Restriction Endonuclease EcoRI of Deoxyoctanucleotides Containing Modified Sugar Moieties", *European Journal of Biochemistry*, 1984, 139, 447–450.

Ikehara, et al., "A Linear Relationship Between Electronegativity of 2'–Substituents and Conformation of Adenine Nucleosides", *Tetrahedron Letters*, 1979, 42, 4073–4076.

Ikehara, et al., "Polynucleotides. LII.synthesis and properties of poly(2'–deoxy–2'–fluoroadenylic acid)" *Nucleic Acids Research*, 1978, 5, 1877–1887.

Ikehara, et al., "Polynucleotides. LVI, Synthesis and Properties of Poly(2'–deoxy–2'–fluoroinosinic Acid)" *Nucleic Acids Research*, 1978, 5, 3315–3324.

Ikehara, et al., "Polynucleotides. L. Synthesis and properties of poly(2'–chloro–2'–deoxyandenylic acid) and poly(2'–bromo–2'–deoxyandenylic acid)", *Nucleic Acids Research*, 1977, 4, 4249–4260.

Eckstein, et al., "Polynucleotides Containing 2'–Chloro–2'–Deoxyribose", *Biochemistry*, 1972, 11, 4336–4344.

Inoue, et al., "Synthesis and hybridization studies on two complementary nona(2'–O–methyl) ribonucleotides", *Nucleic Acids Research*, 1987, 15, 6131–6148.

Shibahara, et al., "Inhibiton of Human Immunodeficiency Virus (HIV–1) Replication by Synthetic Oligo–RNA Derivatives", *Nucleic Acids Research*, 1987, 17, 239–252.

Guschlbauer, et al., "Nucleoside conformation is Determined by the Electronegativity of the Sugar Substituent", *Nucleic Acids Research*, 1980, 8, 1421 (Abstract).

Stein, C.A. and Cohen, J.S., "Oligonucleotides as Inhibitors of Gene Expression", *Cancer Research*, 1988, 48, 2659–2668.

Walder, J., "Antisense DNA and RNA: progress and prospects", *Genes & Devleop.*, 1988, 2, 502–504.

Zon, G., "Synthesis of backbone–modified DNA analogues for biological applications", *J. Protein Chem.*, 1987, 6, 131–145.

Van der Krol, A.R., et al., "Modulation of Eukaryotic Gene Expression by Complementary RNA or DNA Sequences", *BioTechniques*, 1988, 6, 958–973.

Loose, Mitchell, D.S., "Antisense Nucleic Acids as a Potential Class of Pharmaceutical Agents", *TIPS*, 1988, 9, 45–47.

Miller, P.S., et al., "A New Approach to Chemotherapy Based on Molecular Biology and Nucleic Acid Chemistry: Mtagen (Masking Tape for Gene Expression)" *Anti–Cancer Drug Design*, 1987, 2, 117–128.

Walder, R.Y. and Walder, J.A., "Role of RNase H in hybrid–arested translation by antisense oligonucleotides", *Proc. Natl. Acad. Sci. USA*, 1988, 85, 5011–5015.

Stein, C.A., et al., "Physicochemical Properties of Phosphorothioate Oligodeoxynucleotides", *Nucleic Acids Research*, 1988, 16, 3209–3221.

Agarwal, et al., "Synthesis and Enzymatic Properties of Deoxyribooligonucleotides Containing Methyl and Phenylphosphonate Linkages", *Nucleic Acids Research*, 1979, 6, 3009–3024.

Miller, P.S., et al., "Nonionic Nucleic Acid Analogues. Synthesis and Characterization of Dideoxyribonucleoside Methylphosphonates", *Biochemistry*, 1979, 18, 5134–5143.

Jayaraman, K.., "Selective inhibition of *escherichia coli* protein synthesis and growth by nonionic oligonucleotides complementary to the 3'end of 16S rRNA", *Proc. of the Nat. Acad. Sci. USA*, 1981, 78, 1537–1541.

Miller, P.S., et al., "Synthesis and properties of adenine and thymine nucleoside alkyl phosphotriesters, the neutral anlogs of dinucleoside monophosphates", *J. Am. Chem. Soc.*, 1971, 93, 6657–6665.

Agris, C.H., et al., "Inhibition of Vesicular Stomatitis Virus Protein Synthesis and Infection by Sequence–Specific Oligodeoxyribonucleoside Methylphosphonates", *Biochemistry*, 1986, 25, 6268–6275.

Smith, C.C., et al., "Antiviral effect of an oligo(nucleoside methylphosphonate)complementary to the splice junction of herpes simplex virus type 1 immediate early pre–mRNAs 4 and 5", *Proc. Natl. Acad. Sci. USA*, 1986, 83, 2787–2791.

Ruby, S.W., et al., "An early hierarchic role of U1 small nuclear ribonucleoprotein in splicesome assembly", *Science*, 1988, 242, 1028–1035.

Tidd, D.M., et al., "Evaluation of N–ras oncogene anti–sense, sense and nonsense sequence methylphosphonate oligonucleotide analogues", *Anti–Cancer Drug Design*, 1988, 3, 117–127.

HCPF Roelen, et al., "Synthesis of nucleic acid methylphos–phonothioates", *Nucleic Acid Research*, 1988, 16, 7633–7645.

Agarwal, et al., "Oligodeoxynucleoside Phosphoramidtes and Phosphorothioates as Inhibitors of Human Immunodeficiency Virus", *Proc. Natl. Acad. Sci. USA*, 1988, 85, 7079–7083.

Matsukura, M., et al., "Phosphorothioate analogs of oligodeoxynucleotides: Inhibitors of replication and cytopathic effects of human immunodeficiency virus", *Proc. Acad. Sci. USA*, 1987, 84, 7706–7710.

Brill, W.K.D., et al., "Synthesis of oligodeoxynucleoside phosphorodithioates via thioamidites", *J. Am. Chem. Soc.*, 1989, 111, 2321–2322.

Jager, A., et al., "Oligonucleotide N–alkylphosphoramidates: Synthesis and binding to polynucleotides", *Biochemistry*, 1988, 27, 7237–7246.

Cazenave, et al., "Enzymatic amplification of translation inhibition of rabbit βglobin mRNA mediated by anti–messenger oligodeoxynucleotides covalently linked to intercalating agents", *Nucleic Acid Research*, 1987, 15, 4717–4736.

Constant, J.F., et al., "Heterodimeric Molecules Including Nucleic Acid Bases and 9–Aminoacridine Spectroscopic Studies", *Biochemistry*, 1988, 27, 3997–4003.

Yeung, A.T., et al., "Photoreactives and thermal properties of psoralen cross-links", *Biochemistry*, 1988, 27, 3204–3210.

Meyer, R.B., "Efficient, Specific Cross–Linking and Cleavage of DNA by Stable, Synthetic Complementary Oligodeoxynucleotides", *J. Am. Chem. Soc.*, 1989, 111, 8517–8519.

Knorre, D.G. and Vlassov, V.V., "Complementary–addressed (sequence–specific) modification of nucleic acids", *Progress in Nucleic Acid Res. & Mol. Biol.*, 1985, 32, 291–320.

Doan, P.L., et al., Nucleic Acids Res., 1987, 15, 8643–8659.

Sigman D.S., "Nuclease Activity of 1,10–Phenanthroline–Copper Ion", *Accts. Chem. Res.*, 1986, 19, 180–186.

Dreyer, G.B. and Dervan, P.B., "Sequence–specific cleavage of single stranded DNA: Oligodeoxynucleotide–EDTA–Fe(II)", *Proc. Natl. Acad. Sci. USA*, 1985, 82, 968–972.

The Chemistry of Heterocyclic Compounds, A. Weissberger, Ed., Imidazole and Derivatives, Part 1, Interscience, N.Y., 1953.

Biggadike, et al., "Short convergent route to homochiral carbocyclic 2'–deoxynucleosides and carbocyclic robonucleosides", *J. Chem. Soc., Chem., Commun.*, 1987, 1083–1084.

Outten, R.O., and Daves, D., Jr., "Synthetic 1–methoxybenzo[d]naptho[1,2–b]pyran–6–one c–glycosides", *J. Org. Chem.*, 1987, 52, 5064–5066.

Kazimierczuk, Z., et al., "Synthesis of 2–deoxytubercidin, 2'–deoxyadenosine, and related 2'–deoxynucleosides via novel direct stereospecific sodium salt glycosylation procedure", *J. Am. Chem. Soc.*, 1984, 106, 6379–6382.

Revankar, et al., "Synthesis and Antiviral/Antitumor of Certain 3–Seazaguanine Nucleosides and Nucleotides", *J. Med. Chem.*, 1984, 27, 1389–1396.

Stufkens, D.J., "Dynamic Jahn–Teller Effect in the Excited States of $SeCl_6^{2-}$, $SeBr_6^{2-}$, $TeCl_6^{2-}$ and $TeBr_6^{2-}$", *Rec. Trav. Chim.*, 1970, 89, 1185–1201.

Castle, et al., "Imidazo[4,5–D]pyridazines. I. Synthesis of 4,7–disubstituted derivatives", *J. Org. Chem.*, 1958, 23, 1534–1538.

Nucleic Acid Chemistry, Improved and New Synthetic Procedures, Methods and Techniques, Part 3, p. 229, 1986.

Suciu, et al., "Synthesis of 9–(2,5–dideoxy–β–D–glycero–pent–4–enofuranosyl)adenine", *Carbohydr. Res.*, 1975, 44, 112–115.

Jones, R. A., in Oligonucleotide Synthesis—A Practical Approach, M.J. Gait, Ed., IRL Press, Washington, D.C. 1985.

Robins, M.J., et al., "Nucleic acid related compounds. 46. A general procedure for the efficient deoxygenation of secondary alcohols. regiospecific and stereoselective conversion of ribonucleosides to 2'–deoxynucleosides", *J. Am. Chem. Soc.*, 1983, 105, 4059–4065.

Jones, G., "4'–substituted nucleosides. 5. Hydroxymethylation of nucleoside 5'–aldehydes", *J. Org. Chem.*, 1979, 44, 1309–1317.

Arnott, S. And Hukins, D.W.L., "Optimised Parameters for A–DNA and B–DNA" *Biochem. and Biophys. Res. Commun.*, 1970, 47, 1504–1510.

Beaucage, S., et al., "Deoxynucleoside phosphoramidites—A new class of key intermediates for deoxypolynucleotide synthesis", *Tetrahedron Letters*, 1981, 22, 1859–1862.

Beaucage, S., et al., "3H–1,2–Benzodithiole–3–one, 1,1–Dioxide as an Improved Sulfurizing Reagent in the Solid–Phase Synthesis of Olideoxyribonucleoside Phosphorothioates", *J. Am. Chem. Soc.*, 1990, 112, 1253–1254.

Butke, G., Nucleic Acid Chemistry, Part 3: 149–152, Townsend, L.B. and Tipson, R.S., eds., J. Wiley and Sons, New York, 1986.

Caruthers, M., Oligonucleotides: "Antisense Inhibitors of Gene Expression", pp. 7–24, J.S. Cohen, ed., CRC Press, Inc., Boca Raton, FL, 1989.

Chen, Q.Y. and Wu, S.W., J. Chem. Soc. Perkin Trans., 1989, 2385–2387.

Cladek, S., et al., J. Carbohyd., Nucleosides & Nucleotides, 1980, 7, 63–75.

Ikehara, M. And Imura, J., "Studies of Nucleosides and Nucleotides–LXXXII.[1] cyclonucleosides. (39).[2] synthesis and properties fo 2'halogen–2'–deoxyadenosines", *Chem. Pharm. Bull.* 1978, 26, 2449–2453.

Ikehara, M., "Studies of Nucleosides and Nucleotides–LXXIX.[1], Purine cyclonucleosides. (37). The total synthesis of an antibiotic 2'–amino–2'deoxyguanosine[2]", *Chem. Pharm. Bull.*, 1978, 26, 240–244.

De las Heras, F., et al., "3–C–Cyano–3'–Deoxythymidine", *Tetrahedron Letters*, 1988, 29, 941–944.

Fox, J.J., et al., J. Org. Chem., 1964, 29, 558–564.

Freskos, J.N., "Synthesis of 2'Deoxypyrimidine Nucleosides Via Copper", *Nucleosides & Nucleotides*, 1989, 8, 1075–1076.

Gait, M.J., ed., Oligonucleotide Synthesis: A Practical Approach, IRL Press, Washington, D.C., 1984.

Hertel, L.W., et al., "Synthesis of 2–deoxy–2,2–difluoro–D–ribose and 2–deoxy–2,2–difluoro–D–ribofuranosyl nucleosides", *J. Org. Chem.*, 1988, 53, 2406–2409.

Ikehara, M., et al., "Studies of Nucleosides and Nucleotides–LXXIV[1] Purine Cyclonucleosides—34 A New Method for the Synthesis of 2'–substituted 2'deoxyadenosines", *Tetrahedron*, 1978, 34, 1133–1138.

Ikehara, M., et al., "Purine 8–cyclonucleosides", *Accounts of Chemical Research*, 1969, 2, 47–53.

Ikehara, M., et al., "Improved Synthesis of 2'–fluoro–2'–deoxyadenosine and Synthesis and Carbon–13 NMR Spectrum of Its 3',5'–cyclic Phosphate Derivative", *Nucleosides & Nucleotides*, 1983, 2, 373–385.

Ikehara, M. And Imura, J., et al., "Studies of Nucleosides and Nucleotides–LXXXIV. Purine cyclonucleosides. (43). Synthesis and properties of 2'halogen–2'–deoxyguanosine", *Chem. & Pharm. Bull.*, 1981, 29, 3281–3285.

Ikehara, M. And Imura, J., et al., "Studies on Nucleosides and Nucleotides–LXXXVII[1], Purine cyclonucleosides. XLII. Synthesis of 2'deoxy–2'fluorofunaosine", *Chem. & Pharm. Bull.*, 1981, 29, 1034–1038.

Inoue, et al., "Synthesis and hybridization studies on two complementary nona(2'–O–methyl)ribonucleotides" *Nucleic Acids Research*, 1987, 15, 6131–6148.

Jarvi, E.T., et al., "Synthesis and biological evaluation of dideoxunucleosides containing a difluoromethylene unit", *Nucleosides & Nucleotides*, 1989, 8, 1111–1114.

Jones, R.A., "Transient protection: Efficient one–flask synthesis of protected deoxynucleosides", *J. Am. Chem. Soc.*, 1982, 104, 1316–1319.

Koole, L.H., et al., "Synthesis of phosphate–methylated DNA fragments using 9–fluorenylmethoxycarbonyl as transient base protecting group", *J. Org. Chem.*, 1989, 54, 1657–1664.

Markiewicz, W.T. and Wiewiorowski, Nucleic Acid Chemistry, Part 3, pp. 222–231, Townsend, L.B. and Tipson, R.S., eds., J. Wiley & Sons, New York, 1986.

Ogilvie, K.K., Can. J. Chem., 1989, 67, 831–839.

Parkes, K.E.B. and Taylor, B., "A short synthesis of 3'–cyano–3'–Deoxythymidine", *Tetrahedron Letters,* 1988, 29, 2995–2996.

Ranganathan, "Modification of the 2'–Position of Purine Nucleosides: Synthesis of 2'–a–Substituted–2'–Deoxyadenosine Analogs", *Tetrahedron Letters,* 1977, 15, 1291–1294.

Robins, R.K., et al., J. Am. Chem. Soc., 1984, 106, 6379.

Sproat, B.S., et al., "New synthetic routes to protected purine 2'–O–methylriboside–3'–O–phosphoramidites using a novel alkylation procedure", *Nucleic Acids Research,* 1990, 18, 41–49.

Sproat, B.S., et al., "Highly Efficient Chemical Synthesis of 2'–O–Methylioligoribunocleotides and Tetrabiotinylated Derivatives; Novel Probes That are Resistant to Degradation by RNA or DNA Specific Nucleases", *Nucleic Acids Research,* 1989, 17, 3373–3386.

Sakanoue, et al., "Protein Kinase C Activity as Marker for Colorectal Cancer", *Int. J. Cancer,* 1991, 48, 803–806.

Berkowitz, et al., "Synthesis of 1,2–Dihydro–1–(2deoxy–β–D–Erythro–pentafuranosyl)–2–Oxopyrazine 4–oxide, a potent analog of deoxyuridine", *J. Med. Chem.,* 1973, 16(2), 183–184.

Boyce, J. J. et al., "Regulation of Neuronal Differentiation by the a and e Isoforms of Protein Kinase C," Neuroscience Research Communications, Gispen, W.H. et al., John Wiley & Sons, Ltd., 1996, 18, 195–201.

Dean, N. M. et al., "Inhibition of Growth of Xenografted Human Tumor Cell Lines in Nude Mice by an Antisense Oligonucleotide Targeting Human PKC–a," *Proc. Annu. Meet. Am. Assoc. Cancer Res.,* 1995, 36, 413 (Abstract, 2460).

Dooley et al., Phosphorothioate Antisense Oligonucleotide to Protein Kinase C (PKC) Inhibit Proliferation in Rat C6 Glioma, Proceedings of the American Association for Cancer Research 35, 566 (Mar. 1994) (abstract No. 3375).

Gura, T., "Antisense has Growing Pains," *Science,* 1995, 270, 575–577.

Infectious Disease Weekly (Oct. 23, 1995), Charles W. Henderson (Publ.).

Orkin, et al., "Report and Recommendations of the Panel to Assess the NIH Investment in Research on Gene Therapy," 1995, 41 pages.

PR Newswire, Aug. 1, 1996 p. 0801LATH014 (PR Newswire Assoc., Inc.).

Roberts and Caserio Basic Principles of Organic Chemistry, W.A. Benjamin, Inc., New York (1965), 578–79.

Rojanasakul, Y., "Antisense oligonucleotide therapeutics: drug delivery and targeting," *Advanced Drug Delivery Reviews,* 1996, 18, 115–131.

* cited by examiner

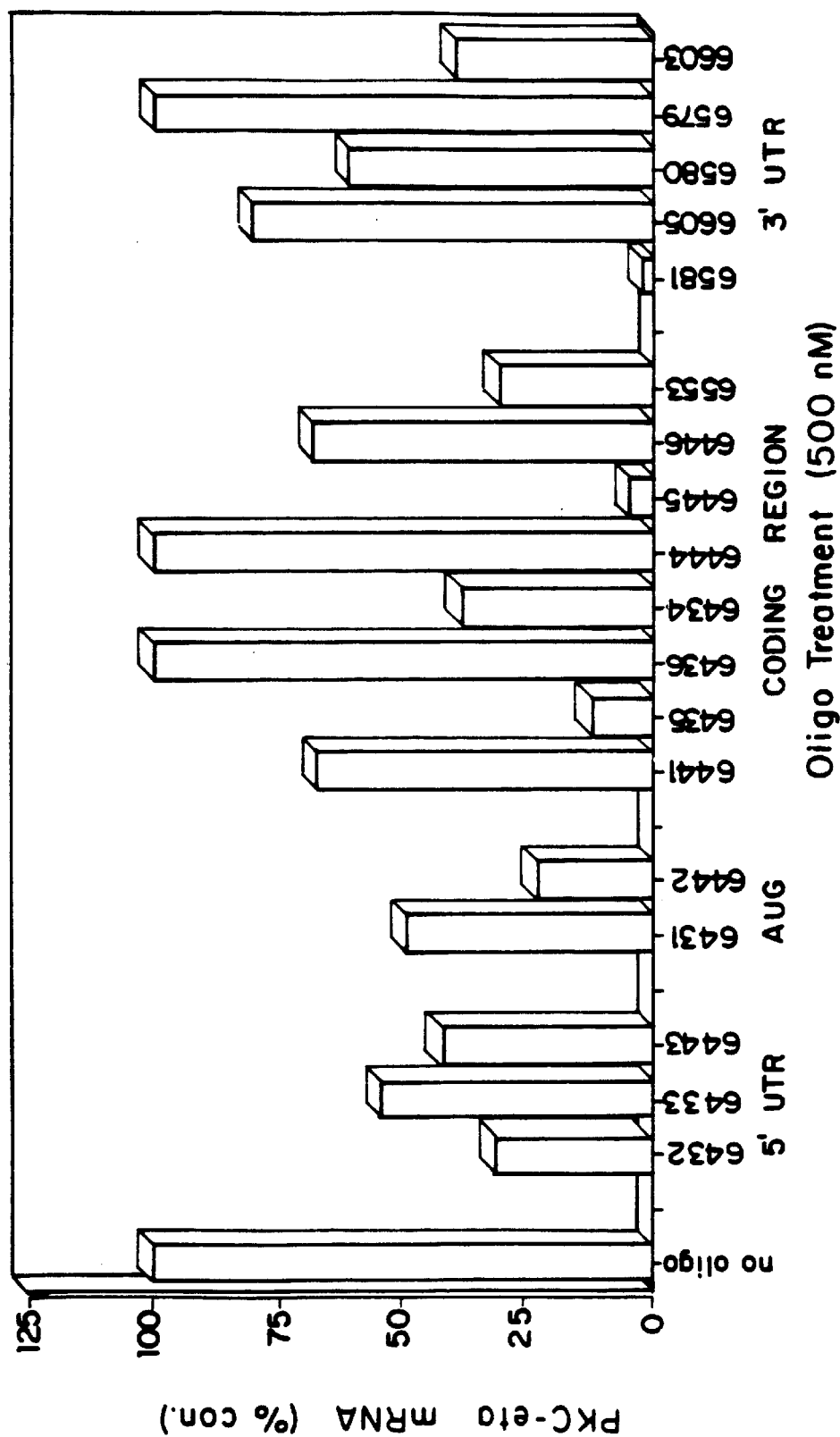

SEQUENCE LISTING

```
<160> NUMBER OF SEQ ID NOS: 121

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
ccccaaccac ctcttgctcc                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gttctcgctg gtgagtttca                                              20

<210> SEQ ID NO 3
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 3
aaaacgtcag ccatggtccc                                               20

<210> SEQ ID NO 4
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 4
ggattcactt ccactgcggg                                               20

<210> SEQ ID NO 5
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 5
gagaccctga acagttgatc                                               20

<210> SEQ ID NO 6
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 6
cccgggaaaa cgtcagccat                                               20

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 7
ctgcctcagc gcccctttgc                                               20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 8
agtcggtgca gtggctggag                                               20

<210> SEQ ID NO 9
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 9
gcagaggctg gggacattga                                               20

```
<210> SEQ ID NO 10
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 10
gggctgggga ggtgtttgtt                                           20

<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 11
cactgcgggg agggctgggg                                           20

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
agccgtggcc ttaaaatttt                                           20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
attttcaggc ctccatatgg                                           20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
aagagagaga ccctgaacag                                           20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
gataatgttc ttggttgtaa                                           20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 16
atggggtgca caaactgggg                                              20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
gtcagccatg gtcccccccc                                              20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
cgccgtggag tcgttgcccg                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
tcaaatggag gctgcccggc                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
tggaatcaga cacaagccgt                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
catcttgcgc gcggggagcc                                              20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
tgcgcgcggg gagccggagc                                              20

<210> SEQ ID NO 23
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 23
cgagaggtgc cggccccggg                                           20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ctctcctcgc cctcgctcgg                                           20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
tggagtttgc attcacctac                                           20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
aaaggcctct aagacaagct                                           20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
gccagcatgt gcaccgtgaa                                           20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28 acacccagg ctcaacgatg                                            20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
```
ccgaagctta ctcacaattt                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
acttagctct tgacttcggg                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
atgctgcgga aaataaattg                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
attttatttt gagcatgttc                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tttggggatg agggtgagca                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cccattccca caggcctgag                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cggagcgcgc caggcaggga                                              20

<210> SEQ ID NO 36
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 36
ccttttccca gaccagccat                                                    20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
ggccccagaa acgtagcagg                                                    20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
ggatcctgcc tttcttgggg                                                    20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
cagccatggc cccagaaacg                                                    20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
cgacatgccg gcgccgctgc                                                    20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
cagacgacat gccggcgccg                                                    20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gcctgcttcg cagcgggaga                                                    20
```

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
acaggtgcag gagtcgaggc                                          20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gtcccgtctc aggccagccc                                          20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
cctcaccgat gcggaccctc                                          20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
attgaacttc atggtgccag                                          20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
tctcactccc cataaggcta                                          20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ttcctttggg ttctcgtgcc                                          20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 49
ttccatcctt cgacagagtt                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
aggctgatgc tgggaaggtc                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gttctaaggc tgatgctggg                                              20

<210> SEQ ID NO 52
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 52
ttctcgctgg tgagtttc                                                18

<210> SEQ ID NO 53
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 53
tctcgctggt gagtttc                                                 17

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
aactcgaggt ggccgccgtc                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
cgccttcgca tagccctttg                                              20

<210> SEQ ID NO 56
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56 ggaagggtg attgcgggcc                                                   20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
aacacgccca ttgcccacca                                                  20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
gtctcaagat ggcgtgctcg                                                  20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
gcgatggttc agctgggccc                                                  20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
gccctctctc tcactcccca                                                  20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ctgggaaggt ccgatagagg                                                  20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
```

```
aaggctgatg ctgggaaggt                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
gcaggaacgg cgccatggtg                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ctggttcgcc tcgtcctcgg                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
atctggatga cgcgcccctc                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
ttcttgcagc gctcggccag                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tgcaatccac gtcctccagg                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ggctccgcgg cggttcatcg                                              20

<210> SEQ ID NO 69
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 69
aagcggtgcg gcatgtcgat                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gcaggctgcc gcagtggtca                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
cctccccagc aactccggtc                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
agcggccttt gtcctggatg                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ggccatcccg gtccaacagc                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ggtgctggcc cggctctccc                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
ggaccccgaa agaccaccag                                              20
```

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
gtggctccaa cctccgcttt                                          20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
aggaggtgct cgaatttggg                                          20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
actaccatgg tcggggcggg                                          20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
gtcccaccgc atggcgcagc                                          20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
gtttggccga tgcgcgagtc                                          20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tgcagttggc cacgaagtcg                                          20

<210> SEQ ID NO 82
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 82
gtggggcatg ttgacgctga                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ccagagcagg gacccacagt                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
tctcctcggt tgtcaaatga                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
cggtgctcct ctcctcggtt                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
agccaaaatc ctcttctctg                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
catgagggcc gatgtgacct                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
atcccttcct tgcacatccc                                               20
```

```
<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ccccagggcc caccagtcca                                                   20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
agcaccccca gggcccacca                                                   20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
cgtacatcag caccccagg                                                    20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
ccagccatca tctcgtacat                                                   20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
tgccacacag cccaggcgca                                                   20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
tcagggcatc aggtcttcac                                                   20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 95
ctctcagggc atcaggtctt                                           20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
aaggaaagtc tgcggccggg                                           20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
tggcggctcc cgttctgcag                                           20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
gcttcctcgg ccgcatgcgt                                           20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ttgacgctga accgctggga                                           20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
gcccggtgct cctctcctcg                                           20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
gggccgatgt gacctctgca                                           20

<210> SEQ ID NO 102
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 102
tggaggaaca tgagggccga                                                 20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
cccccagggc ccaccagtcc                                                 20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
tgcgatgcca cacagcccag                                                 20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
tgggctctca gggcatcagg                                                 20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
cgccgctccc ttccatcttg                                                 20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
ccccgtaatg cgccttgagg                                                 20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
```

-continued ctgtccaccc acttgagggt     20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
ttggaagagg tggccgttgg     20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
cctgttaaag cgcttggctt     20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
tgcaggtcag cgggacgagg     20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
agcccctgag agattttgat     20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
ttcttcaacc gcaccaggag     20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
tccttgcaca tgccgtagtc     20

<210> SEQ ID NO 115
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 115
ggagcgcccg gccatcatct                                               20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
gggctcgctg gtgaactgtg                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
gacgcacgcg gcctcacacc                                               20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
tcggagccgt gcccagcctg                                               20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
cgggccaggt gtgagggact                                               20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
ccgcgacgca ggcacagcag                                               20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
ggtcagtgca tcgagttctg                                               20
```

OLIGONUCLEOTIDE INHIBITION OF PROTEIN KINASE C

CROSS REFERENCE TO RELATED APPLICATIONS

This application is a continuation-in-part of U.S. patent application Ser. No. 08/829,637, filed Mar. 31, 1997, now U.S. Pat. No. 6,339,066, which is a continuation-in-part of U.S. patent application Ser. No. 08/478,178, filed Jun. 7, 1995 (U.S. Pat. No. 5,882,927), which is a continuation-in-part of U.S. patent application Ser. No. 08/089,996, filed Jul. 9, 1993, (U.S. Pat. No. 5,703,054) which is a continuation-in-part of U.S. patent application Ser. No. 07/852,852, filed Mar. 16, 1992, now abandoned.

FIELD OF THE INVENTION

This invention relates to therapies, diagnostics, and research reagents for disease states which respond to modulation of the expression of protein kinase C. In particular, this invention relates to antisense oligonucleotides specifically hybridizable with nucleic acids relating to protein kinase C. These oligonucleotides have been found to modulate the expression of protein kinase C.

BACKGROUND OF THE INVENTION

The phosphorylation of proteins plays a key role in the transduction of extracellular signals into the cell. The enzymes, called kinases, which effect such phosphorylations are targets for the action of growth factors, hormones, and other agents involved in cellular metabolism, proliferation and differentiation. One of the major signal transduction pathways involves the enzyme protein kinase C (PKC), which is known to have a critical influence on cell proliferation and differentiation. PKC is activated by diacylglycerols (DAGs), which are metabolites released in signal transduction.

Interest in PKC was stimulated by the finding that PKC is the major, and perhaps only, cellular receptor through which a class of tumor-promoting agents called phorbol esters exert their pleiotropic effects on cells [Gescher et al., *Anti-Cancer Drug Design* 4:93–105 (1989)]. Phorbols capable of tumor production can mimic the effect of DAG in activating PKC, suggesting that these tumor promoters act through PKC and that activation of this enzyme is at least partially responsible for the resulting tumorigenesis [Parker et al., *Science* 233:853–866 (1986)].

Experimental evidence indicates that PKC plays a role in growth control in colon cancer. It is believed that specific bacteria in the intestinal tract convert lipids to DAG, thus activating PKC and altering cell proliferation. This may explain the correlation between high dietary fat and colon cancer [Weinstein, *Cancer Res.* (*Suppl.*) 51:5080s–5085s (1991)]. It has also been demonstrated that a greater proportion of the PKC in the colonic mucosa of patients with colorectal cancer is in an activated state compared to that of patients without cancer [Sakanoue et al., *Int. J. Cancer* 48:803–806 (1991)].

Increased tumorigenicity is also correlated with overexpression of PKC in cultured cells inoculated into nude mice. A mutant form of PKC induces highly malignant tumor cells with increased metastatic potential. Sphingosine and related inhibitors of PKC activity have been shown to inhibit tumor cell growth and radiation-induced transformation in vivo [Endo et al., *Cancer Research* 51:1613–1618 (1991); Borek et al., *Proc. Natl. Acad. Sci.* 88:1953–1957 (1991)]. A number of experimental or clinically useful anti-cancer drugs show modulatory effects on PKC. Therefore, inhibitors of PKC may be important cancer-preventive or therapeutic agents. PKC has been suggested as a plausible target for more rational design of conventional anti-cancer drugs [Gescher, A. and Dale, I. L., *Anti-Cancer Drug Design*, 4:93–105 (1989)].

Experiments also indicate that PKC plays an important role in the pathophysiology of hyperproliferative skin disorders such as psoriasis and skin cancer. Psoriasis is characterized by inflammation, hyperproliferation of the epidermis and decreased differentiation of cells. Various studies indicate a role for PKC in causing these symptoms. PKC stimulation in cultured keratinocytes can be shown to cause hyperproliferation. Inflammation can be induced by phorbol esters and is regulated by PKC. DAG is implicated in the involvement of PKC in dermatological diseases, and is formed to an increased extent in psoriatic lesions. Inhibitors of PKC have been shown to have both antiproliferative and anti-inflammatory effects in vitro. Some antipsoriasis drugs, such as cyclosporine A and anthralin, have been shown to inhibit PKC. Inhibition of PKC has been suggested as a therapeutic approach to the treatment of psoriasis [Hegemann, L. and G. Mahrle, *Pharmacology of the Skin*, H. Mukhtar, ed., p. 357–368, CRC Press, Boca Raton, Fla., 1992].

The oligonucleotides of the invention are useful in the therapeutic treatment of diseases associated with PKC. Such diseases include hyperproliferative and inflammatory conditions including psoriasis, tumors and cancers, for example glioblastoma, bladder cancer, breast cancer, lung cancer, colon cancer, ovarian cancer and pancreatic cancer.

PKC is not a single enzyme, but a family of enzymes. At the present time at least seven isoforms (isozymes) of PKC have been identified: isoforms $\alpha$, $\beta$, and $\gamma$ have been purified to homogeneity, and isoforms $\delta$, $\epsilon$, $\zeta$ and $\eta$ have been identified by molecular cloning. These isozymes have distinct patterns of tissue and organ localization (see Nishizuka, *Nature*, 334:661–665 (1988) for review) and may serve different physiological functions. For example, PKC-$\gamma$ seems to be expressed only in the central nervous system. PKC-$\alpha$ and -$\beta$ are expressed in most tissues, but have different patterns of expression in different cell types. For example, both PKC-$\alpha$ and PKC-$\beta$ are expressed in, and have been purified from, human epidermis. While PKC-$\alpha$ has been detected mainly in keratinocytes of the basal layers of the epidermis, PKC-$\beta$ is found mainly in the middle layers of the epidermis and Langerhans cells. PKC-$\eta$ has been found predominantly in the skin and lungs, with levels of expression much higher in these tissues than in the brain. This is in contrast to other members of the PKC family which tend to be most abundantly expressed in the brain [Osada et al., *J. Biol. Chem.* 265:22434–22440 (1990)]. While the PKC isozymes listed here are preferred for targeting by the present invention, other isozymes of PKC are also comprehended by the present invention.

It is presently believed that different PKC isozymes may be involved in various disease processes depending on the organ or tissue in which they are expressed. For example, in psoriatic lesions there is an alteration in the ratio between PKC-$\alpha$ and PKC-$\beta$, with preferential loss of PKC-$\beta$ compared to normal skin [Hegemann, L. and G. Mahrle, *Pharmacology of the Skin*, H. Mukhtar, ed., p. 357–368, CRC Press, Boca Raton, Fla., 1992].

Although numerous compounds have been identified as PKC inhibitors (see Hidaka and Hagiwara, *Trends in Pharm.*

Sci. 8:162–164 (1987) for review), few have been found which inhibit PKC specifically. While the quinoline sulfonamide derivatives such as 1-(5-isoquinolinesulfonyl)-2-methylpiperazine (H-7) inhibit PKC at micromolar concentrations, they exhibit similar enzyme inhibition kinetics for PKC and the CAMP-dependent and cGMP-dependent protein kinases. Staurosporine, an alkaloid product of Streptomyces sp., and its analogs, are the most potent in vitro inhibitors of PKC identified to date. However, they exhibit only limited selectivity among different protein kinases [Gescher, *Anti-Cancer Drug Design* 4:93–105 (1989)]. Certain ceramides and sphingosine derivatives have been shown to have PKC inhibitory activity and to have promise for therapeutic uses, however, there remains a long-felt need for specific inhibitors of the enzymes.

There is also a desire to inhibit specific PKC isozymes, both as a research tool and in diagnosis and treatment of diseases which may be associated with particular isozymes. Godson et al. [*J. Biol. Chem.* 268:11946–11950 (1993)] disclosed use of stable transfection of antisense PKC-α cDNA in cytomegalovirus promotor-based expression vectors to specifically decrease expression of PKC-α protein by approximately 70%. It was demonstrated that this inhibition caused a loss of phospholipase $A_2$-mediated arachidonic acid release in response to the phorbol ester PMA. Attempts by the same researchers at inhibiting PKC activity with oligodeoxynucleotides were ultimately unsuccessful due to degradation of oligonucleotides. Ahmad et al. disclose that transfection of the human glioblastoma cell line, U-87, with vectors expressing antisense RNA to PKCα inhibits growth of the glioblastoma cells in vitro and in vivo. Ahmad et al., 1994, Neurosurg. 35:904–908. Diaz-Meco Conde et al. disclose a peptide corresponding to the pseudo-substrate region of PKC-ζ and oligonucleotides antisense to this isozyme. WO Application 93/20101. Alvaro et al. have identified a novel mutant form of PKC associated with tumors and disclose oligonucleotide sequences complementary to the mutant form. WO Application 94/29455.

BRIEF DESCRIPTION OF THE DRAWINGS

FIG. 9 is a set of bar graphs showing the effect of additional oligonucleotides on PKC-α mRNA levels.

FIG. 11 is a set of line graphs showing effect of oligonucleotides on growth of human MDA-MB231 tumors in nude mice.

FIG. 12 is a bar graph showing effect of 20-mer phosphorothioate oligonucleotides on PKC-η expression in A549 cells.

SUMMARY OF THE INVENTION

Figure 1A:
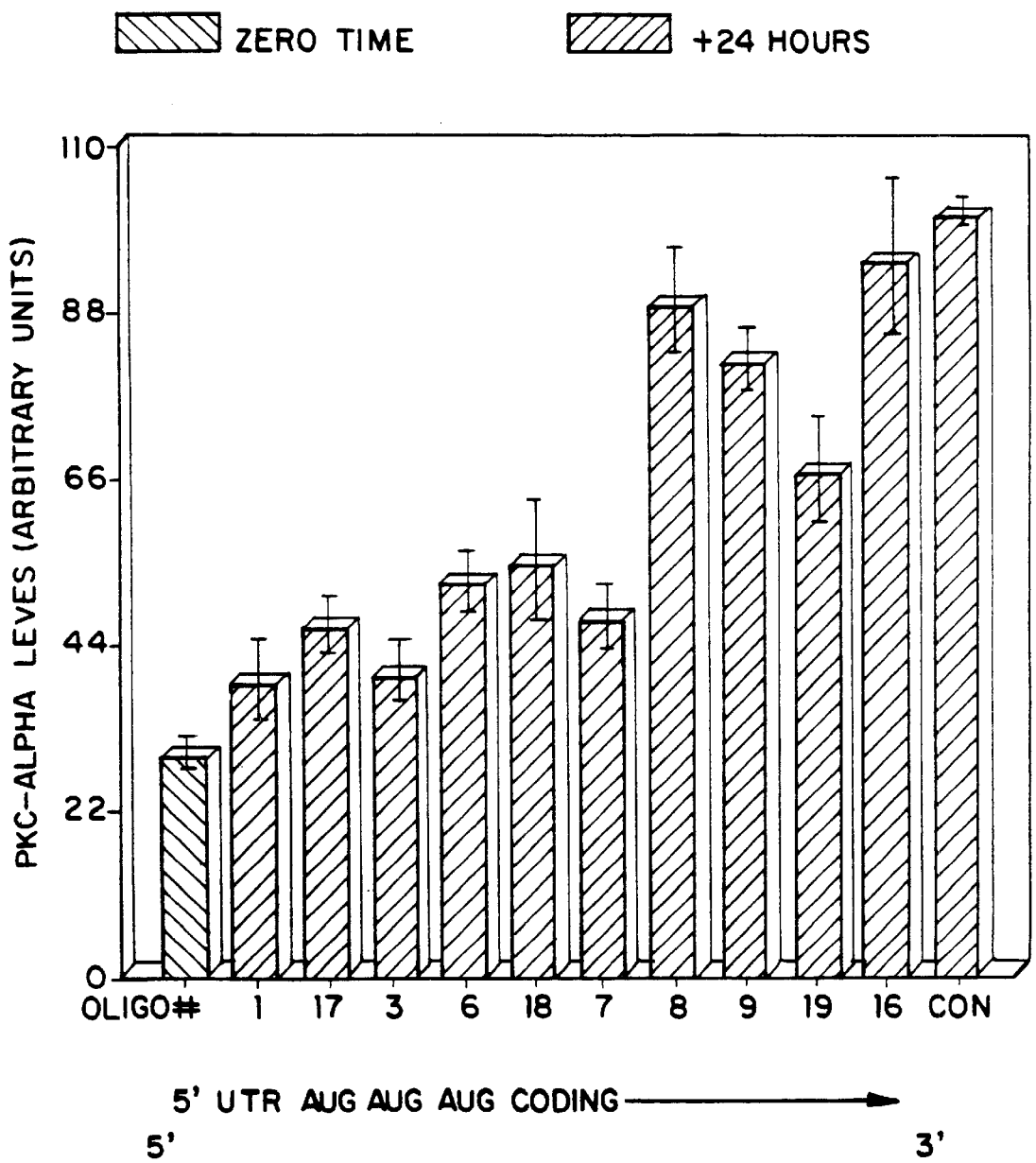
FIGS. 1(*a*) and 1(*b*) are graphical depictions of the effects on PKC expression of antisense oligonucleotides hybridizable with PKC-α. Oligonucleotides are arranged by PKC target region, 5' to 3'.

In accordance with the present invention, oligonucleotides are provided that are specifically hybridizable with a nucleic acid that encodes PKC. This relationship is commonly denominated as "antisense". In a preferred embodiment, oligonucleotides are provided that are specifically hybridizable with a nucleic acid encoding a particular PKC isozyme or a particular set of PKC isozymes. Such oligonucleotides may be conveniently and desirably presented in a pharmaceutically acceptable carrier and may be combined with another chemotherapeutic agent.

In accordance with preferred embodiments, the oligonucleotides comprise one or more chemical modifications which convey some desired characteristic such as improved target affinity, cellular uptake or stability in the presence of cellular nucleases. Examples of modifications having such utility are 2'-O-alkyl and 2'-fluoro sugar modifications and phosphorothioate backbone modifications.

Also provided are methods for modulating the expression of PKC using the oligonucleotides of the invention. Such methods comprise contacting cells or tissues suspected of containing said gene with oligonucleotides in accordance with the invention. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

Other aspects of the invention are directed to methods for diagnostics and therapeutics of animals suspected of having a disease associated with PKC or one of its isozymes.

DETAILED DESCRIPTION OF THE INVENTION

Oligonucleotides have been employed as therapeutic moieties for the treatment of disease states in animals and man. For example, workers in the field have now identified antisense, triplex and other oligonucleotide compositions which are capable of modulating expression of genes implicated in viral, fungal and metabolic diseases.

As examples, U.S. Pat. No. 5,135,917, issued Aug. 4, 1992, provides antisense oligonucleotides that inhibit human interleukin-1 receptor expression. U.S. Pat. No. 5,098,890, issued Mar. 24, 1992 in the name of Gewirtz et al., is directed to antisense oligonucleotides complementary to the c-myb oncogene and antisense oligonucleotide therapies for certain cancerous conditions. U.S. Pat. No. 5,087,617, issued Feb. 11, 1992, provides methods for treating cancer patients with antisense oligonucleotides. U.S. Pat. No. 5,166,195 issued Nov. 24, 1992, provides oligonucleotide inhibitors of HIV. U.S. Pat. No. 5,004,810, issued Apr. 2, 1991, provides oligomers capable of hybridizing to herpes simplex virus Vmw65 mRNA and inhibiting replication. U.S. Pat. No. 5,194,428, issued Mar. 16, 1993, provides antisense oligonucleotides having antiviral activity against influenza virus. U.S. Pat. No. 4,806,463, issued Feb. 21, 1989, provides antisense oligonucleotides and methods using them to inhibit HTLV-III replication. U.S. Pat. No. 5,286,717 (Cohen et al.), issued Feb. 15, 1994, is directed to a mixed linkage oligonucleotide phosphorothioates complementary to an oncogene; U.S. Pat. No. 5,276,019 and U.S. Pat. No. 5,264,423 (Cohen et al.) are directed to phosphorothioate oligonucleotide analogs used to prevent replication of foreign nucleic acids in cells. Antisense oligonucleotides have been safely administered to humans and clinical trials of several antisense oligonucleotide drugs, targeted both to viral and cellular gene products, are presently underway. The phosphorothioate oligonucleotide, ISIS 2922, has been shown to be effective against cytomegalovirus retinitis in AIDS patients. *Bio World Today*, Apr. 29, 1994, p. 3. It is thus established that oligonucleotides can be useful therapeutic instrumentalities and can be configured to be useful in treatment regimes for treatment of cells and animal subjects, especially humans.

Current agents which modulate the activity or metabolism of protein kinase C exhibit many unacceptable side effects due to their lack of specificity, or they exhibit only limited effectiveness in inhibiting the enzyme. The instant invention circumvents problems encountered by prior workers by modulating the production of the enzyme, rather than inhibiting the enzyme directly, to achieve the therapeutic effect. In the instant invention, the oligonucleotide is designed to bind directly to mRNA or to a gene, ultimately modulating the amount of PKC protein made from the gene.

This relationship between an oligonucleotide and its complementary nucleic acid target to which it hybridizes is commonly referred to as "antisense". "Targeting" an oligonucleotide to a chosen nucleic acid target, in the context of this invention, is a multi-step process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding PKC; in other words, a PKC gene or mRNA expressed from a PKC gene. The targeting process also includes determination of a site or sites within the nucleic acid sequence for the oligonucleotide interaction to occur such that the desired effect—modulation of gene expression—will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of PKC gene expression is presently the preferred form of modulation. This modulation can be measured in ways which are routine in the art, for example by Northern blot assay of mRNA expression or Western blot assay of protein expression as taught in the examples of the instant application. Effects on cell proliferation or tumor cell growth can also be measured, as taught in the examples of the instant application.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In the context of this invention, the term "oligonucleotide" refers to a polynucleotide formed from naturally occurring nucleobases and pentofuranosyl (sugar) groups joined by native phosphodiester bonds. This term effectively refers to naturally occurring species or synthetic species formed from naturally occurring subunits or their close homologs.

The term "oligonucleotide" may also refer to moieties which function similarly to naturally occurring oligonucleotides but which have non-naturally occurring portions. Thus, oligonucleotides may have altered sugar moieties, nucleobases or inter-sugar ("backbone") linkages. Such modified or substituted oligonucleotides are often preferred over native forms because of properties such as, for example, enhanced cellular uptake, enhanced target binding affinity and increased stability in the presence of nucleases.

Specific examples of some preferred oligonucleotides envisioned for this invention are those which contain intersugar backbone linkages such as phosphotriesters, methyl phosphonates, short chain alkyl or cycloalkyl intersugar linkages or short chain heteroatomic or heterocyclic intersugar linkages. Most preferred are phosphorothioates and those with $CH_2$—NH—O—$CH_2$, $CH_2$—N($CH_3$)—O—$CH_2$ (known as the methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Phosphorothioates are also most preferred. Also preferred are oligonucleotides having morpholino backbone structures. Summerton, J. E. and Weller, D. D., U.S. Pat. No. 5,034,506. In other preferred embodiments, such as the peptide nucleic acid (PNA— referred to by some as "protein nucleic acid") backbone, the phosphodiester backbone of the oligonucleotide may be replaced with a polyamide backbone wherein nucleosidic bases are bound directly or indirectly to aza nitrogen atoms or methylene groups in the polyamide backbone. see, e.g., P. E. Nielsen, M. Egholm, R. H. Berg, O. Buchardt, *Science* 1991, 254, 1497 and U.S. patent application Ser. No. 08/054,363, filed Apr. 26, 1993 and incorporated herein by reference. In accordance with other preferred embodiments, the phosphodiester bonds are substituted with structures which are chiral and enantiomerically specific. Persons of ordinary skill in the art will be able to select other linkages for use in practice of the invention.

Oligonucleotides may also include species which include at least one modified nucleotide base. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

Chimeric or "gapped" oligonucleotides are also preferred embodiments of the invention. These oligonucleotides contain two or more chemically distinct regions, each comprising at least one nucleotide. Typically, one or more region comprises modified nucleotides that confer one or more beneficial properties, for example, increased nuclease resistance, increased uptake into cells or increased binding affinity for the RNA target. One or more unmodified or differently modified regions retains the ability to direct RNase H cleavage. Chimeric oligonucleotides are disclosed in PCT application US92/11339 which is assigned to the assignee of the instant application and which is incorporated by reference herein in its entirety. Examples of chimeric oligonucleotides which are presently preferred are 2'-O-methyl or 2'-O-propyl oligonucleotides having a "deoxy gap" region of 2'-deoxynucleotides. Usually this deoxy gap region is located between the two 2'-alkyl regions. In these preferred embodiments, the internucleotide (backbone) linkages may be uniformly phosphorothioate or some combination of phosphorothioate and phosphodiester linkages.

Affinity of an oligonucleotide for its target (in this case a nucleic acid encoding PKC) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In one embodiment, the region of the oligonucleotide which is modified to increase PKC mRNA binding affinity comprises at least one nucleotide modified at the 2' position of the sugar, most preferably a 2'-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of PKC gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

All such oligonucleotides are best described as being functionally interchangeable with natural oligonucleotides (or synthesized oligonucleotides along natural lines), but having one or more differences from natural structure. All such oligonucleotides are comprehended by this invention so long as they function effectively to hybridize with the PKC RNA.

The oligonucleotides in accordance with this invention preferably comprise from about 5 to about 50 nucleotide units. As will be appreciated, a nucleotide unit is a base-sugar combination (or a combination of analogous structures) suitably bound to an adjacent nucleotide unit through phosphodiester or other bonds forming a backbone structure.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as phosphorothioates or alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides. Other modified and substituted oligomers can be similarly synthesized.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, a 5' cap region, an intron/exon junction, coding sequences or sequences in the 5'- or 3'-untranslated region.

The oligonucleotides of this invention are designed to be hybridizable with messenger RNA derived from the PKC gene. Such hybridization, when accomplished, interferes with the normal roles of the messenger RNA to cause a modulation of its function in the cell. The functions of messenger RNA to be interfered with may include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to modulate expression of the PKC gene.

The oligonucleotides of this invention can be used in diagnostics, therapeutics, prophylaxis, and as research reagents and kits. Since the oligonucleotides of this invention hybridize to the PKC gene and its mRNA, sandwich and other assays can easily be constructed to exploit this fact. Furthermore, since the oligonucleotides of this invention hybridize specifically to particular isozymes of the PKC mRNA, such assays can be devised for screening of cells and tissues for particular PKC isozymes. Such assays can be utilized for diagnosis of diseases associated with various PKC forms. Provision of means for detecting hybridization of oligonucleotide with the PKC gene can routinely be accomplished. Such provision may include enzyme conjugation, radiolabelling or any other suitable detection systems. Kits for detecting the presence or absence of PKC may also be prepared.

The present invention is also suitable for diagnosing abnormal proliferative states in tissue or other samples from patients suspected of having a hyperproliferative disease such as cancer or psoriasis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. Similarly, the present invention can be used to distinguish PKC-associated tumors, particularly tumors associated with a particular PKC isozyme, from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The oligonucleotides of the invention are also useful for detection and diagnosis of PKC expression, particularly the specific expression of individual isozymes of PKC. For example, radiolabeled oligonucleotides can be prepared by $^{32}$P labeling at the 5' end with polynucleotide kinase. Sambrook et al., *Molecular Cloning. A Laboratory Manual*, Cold Spring Harbor Laboratory Press, 1989, Volume 2, p. 10.59. Radiolabeled oligonucleotides are then contacted with tissue or cell samples suspected of PKC expression and the sample is washed to remove unbound oligonucleotide. Radioactivity remaining in the sample indicates bound oligonucleotide (which in turn indicates the presence of PKC) and can be quantitated using a scintillation counter or other routine means. Radiolabeled oligo can also be used to perform autoradiography of tissues to determine the localization, distribution and quantitation of PKC expression for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing raf. Quantitation of the silver grains permits PKC expression to be detected.

Analogous assays for fluorescent detection of PKC expression can be developed using oligonucleotides of the invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va. See 1993 Catalog of Products for DNA Research, Glen Research, Sterling Va., p. 21).

Each of these assay formats is known in the art. One of skill could easily adapt these known assays for detection of raf expression in accordance with the teachings of the invention providing a novel and useful means to detect PKC expression, particularly of specific PKC isozymes.

For therapeutic or prophylactic treatment, oligonucleotides are administered in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, anti-inflammatory agents, anesthetics, and the like in addition to oligonucleotides. One or more chemotherapeutic agents may also be included. Examples of such agents are anticancer and cytotoxic drugs well-known in the arts include, but are not limited to, daunorubicin, daunomycin, dactinomycin, doxorubicin, epirubicin, idarubicin, esorubicin, bleomycin, magosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydrosyperoxycyclophosphoramide, 5-fluorouracil (5-FU), 5-fluorodeoxyuridine (5-FudR), methotrexate (MTX), colchicine, paclitaxel (taxol), vincristine, vinblastine, etoposide (VP-16), trimetrexate, irinotecam, topotecan, gemcitabine, teniposide, cisplatinum, cisplatin, diethylstilbestrol (DES), docetaxel, leucovorin and carboplatin. See, generally, *The Merck Manual of Diagnosis and Therapy*, 15$^{th}$ Ed., 1987, pp. 1206–1228, Berkow et al., Eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs including but not limited to ribivirin, vidarabine, acyclovir and ganciclovir, may also be combined in compositions of the invention. See, generally, *The Merck Manual of Diagnosis and Therapy*, 15$^{th}$ Ed., Berkow et al., eds., 1987, Rahway, N.J., pp. 2499–2506 and 46–49, respectively). Other non-antisense chemotherapeutic agents are also within the scope of the present invention. Two or more combined compounds may be used together or sequentially.

The pharmaceutical composition may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or by intravenous, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates. Optimum dosages may vary depending on the relative potency of individual oligonucleotides, and can generally be calculated based on EC50's in in vitro and in vivo animal studies. For example, given the molecular weight of compound (derived from oligonucleotide sequence and chemical structure) and an effective dose such as an IC50, for example (derived experimentally), a dose in mg/kg is routinely calculated. Thus, in the context of this invention, by "therapeutically effective amount" is meant the amount of the compound which is required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, if the disease to be treated is psoriasis, a reduction or ablation of the skin plaque is an indication that the administered dose has a therapeutic effect. Similarly, in mammals being treated for cancer, therapeutic effects are assessed by measuring the rate of growth or the size of the tumor, or by measuring the production of compounds such as cytokines, which production is an indication of the progress or regression of the tumor.

The following examples illustrate the present invention and are not intended to limit the same.

EXAMPLES

Example 1

Oligonucleotide Synthesis:

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized according to the procedures set forth above substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'-O-propyl phosphorothioate oligonucleotides may be prepared by slight modifications of this procedure. 2'-fluoro phosphorothioate oligonucleotides were synthesized using 5'-dimethoxytrityl-3'-phosphoramidites and prepared as disclosed in U.S. patent application Ser. No. 463,358, filed Jan. 11, 1990, and 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0.

The oligonucleotides tested are presented in Table 1. Sequence data are from the CDNA sequence published by Finkenzeller et al., *Nucl. Acids Res.* 18:2183 (1990); Genbank accession number X52479. The sequence numbers given under the oligonucleotides are relative to the first residue to be sequenced on the CDNA, which is 28 residues upstream of the ATG start codon.

TABLE 1

OLIGONUCLEOTIDES TARGETED TO HUMAN PKC-α

| SEQ ID | Sequence | Target | ISIS # |
|---|---|---|---|
| 1 | CCC CAA CCA CCT CTT GCT CC<br>19                        1 | 5' Untranslated | 3520 |
| 2 | GTT CTC GCT GGT GAG TTT CA<br>2063                   2044 | 3' Untranslated | 3521 |
| 3 | AAA ACG TCA GCC ATG GTC CC<br>41                       22 | Translation init. codon | 3522 |
| 4 | GGA TTC ACT TCC ACT GCG GG<br>2109                   2090 | 3' Untranslated | 3526 |
| 5 | GAG ACC CTG AAC AGT TGA TC<br>2211                   2192 | 3' Untranslated | 3527 |
| 6 | CCC GGG AAA ACG TCA GCC AT<br>47                       28 | Translation init codon | 3674 |
| 7 | CTG CCT CAG CGC CCC TTT GC<br>110                      91 | Internal (C1)domain | 3682 |
| 8 | AGT CGG TGC AGT GGC TGG AG<br>193                     174 | Internal (C1)domain | 3686 |
| 9 | GCA GAG GCT GGG GAC ATT GA<br>480                     461 | Internal (C1)domain | 3687 |
| 10 | GGG CTG GGG AGG TGT TTG TT<br>2080                   2061 | 3' Untranslated | 3695 |
| 11 | CAC TGC GGG GAG GGC TGG GG<br>2098                   2079 | 3' Untranslated | 3875 |
| 12 | AGC CGT GGC CTT AAA ATT TT<br>2137                   2118 | 3' Untranslated | 3878 |
| 13 | ATT TTC AGG CCT CCA TAT GG<br>2168                   2149 | 3' Untranslated | 3879 |
| 14 | AAG AGA GAG ACC CTG AAC AG<br>2217                   2198 | 3' Untranslated | 3884 |
| 15 | GAT AAT GTT CTT GGT TGT AA<br>2235                   2216 | 3' Untranslated | 3885 |
| 16 | ATG GGG TGC ACA AAC TGG GG<br>2027                   2008 | Internal (C3) domain | 3886 |
| 17 | GTC AGC CAT GGT CCC CCC CC<br>36                       17 | Translation init. codon | 3890 |
| 18 | CGC CGT GGA GTC GTT GCC CG<br>63                       44 | Internal (V1) domain | 3891 |
| 19 | TCA AAT GGA GGC TGC CCG GC<br>1643                   1624 | Internal (C3) domain | 3892 |
| 20 | TGG AAT CAG ACA CAA GCC GT<br>2151                   2132 | 3' Untranslated | 3947 |

Example 2
Cell Culture and Treatment with Phorbol Esters and Oligonucleotides Targeted to PKC-α:

PKC protein half-lives have been reported to vary from 6.7 hours to over 24 hours [Young et al., *Biochem. J.* 244:775–779 (1987); Ballester et al., *J. Biol. Chem.* 260:15194–15199 (1985)]. These long half-lives make inhibiting steady-state levels of PKC-α an unwieldy approach when screening antisense oligonucleotides, due to the long incubation times which would be required. We have therefore made use of the ability of phorbol esters to reversibly lower intracellular levels of PKC. Treatment of cells with phorbol esters causes an initial activation of kinase activity, followed by a down-regulation of PKC. For PKC-α this down-regulation has been shown to be a direct consequence of an increased rate of proteolysis of the kinase with no apparent change in synthetic rate.

We determined that in human lung carcinoma (A549) cells, treatment with the phorbol ester 12,13-dibutyrate (PDBu), using a modification of the method of Krug et al., [Krug et al., *J. Biol. Chem.* 262:11852–11856 (1987)] lowered cellular levels of PKC-α, without affecting PKC-α mRNA levels, and that this effect was reversible. The basis of the assay to screen for potency of oligonucleotides targeting PKC-α is to initially lower PKC-α protein levels by chronic treatment with PDBu, remove PDBu by extensively washing the cells (hence allowing the cells to synthesize fresh PKC-α protein), and incubate the cells with oligonucleotides intended to inhibit the resynthesis of new PKC-α protein.

Procedure: A549 cells (obtained from the American Type Culture Collection, Bethesda Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.).

Cells were treated with 500 nM PDBu (Sigma Chem. Co., St. Louis, Mo.) for 12–16 hours (overnight). Cells were then washed three times in DME at 37° C., and 1 ml DMA containing 20 μl DOTMA (Lipofectin reagent, BRL, Bethesda, Md.) was added. Oligonucleotides were added to a concentration of 1 μM and the cells were incubated for a further 4 hours at 37° C.

Cells were washed once in 3 ml DME containing 0.1 mg/ml BSA and a further 2 ml DME containing 0.1 mg/ml BSA was added. Oligonucleotides (1 μM) were added and the cells were incubated at 37° C. for 24 hours.

Cells were washed three times in phosphate-buffered saline (PBS) and cellular proteins were extracted in 120 μl sample buffer (60 mM Tris pH 6.8, 2% SDS, 10% glycerol, 10 mM dithiothreitol) and boiled for 5 minutes. Intracellular levels of PKC-α protein were determined by immunoblotting.

Example 3
Immunoblot Assay for PKC Expression:

Cell extracts were electrophoresed on 10% SDS-PAGE mini-gels. The resolved proteins were transferred to Immobilon-P membrane (Millipore, Bedford Mass.) by electrophoretic transfer and the membrane was blocked for 60 minutes in TBS (Tris-HCl pH 7.4, 150 mM NaCl) containing 5% nonfat milk. The membrane was then incubated for 16 hours at 4° C. with monoclonal antibodies raised against PKC-α (UBI, Lake Placid N.Y.) diluted to 0.2 μg/ml in TBS containing 0.2% nonfat milk. This was followed by three washes in TBS plus 0.2% nonfat milk. The membrane was then incubated for one hour with $^{125}$I-labelled goat anti-mouse secondary antibody (ICN Radiochemicals, Irvine Calif.). Membranes were then washed extensively in TBS plus 0.2% nonfat milk. Bands were visualized and quantitated using a Phosphorimager (Molecular Dynamics, Sunnyvale, Calif.). PKC-α appears as a single band with a molecular weight of 80 kD.

Figure 1B:
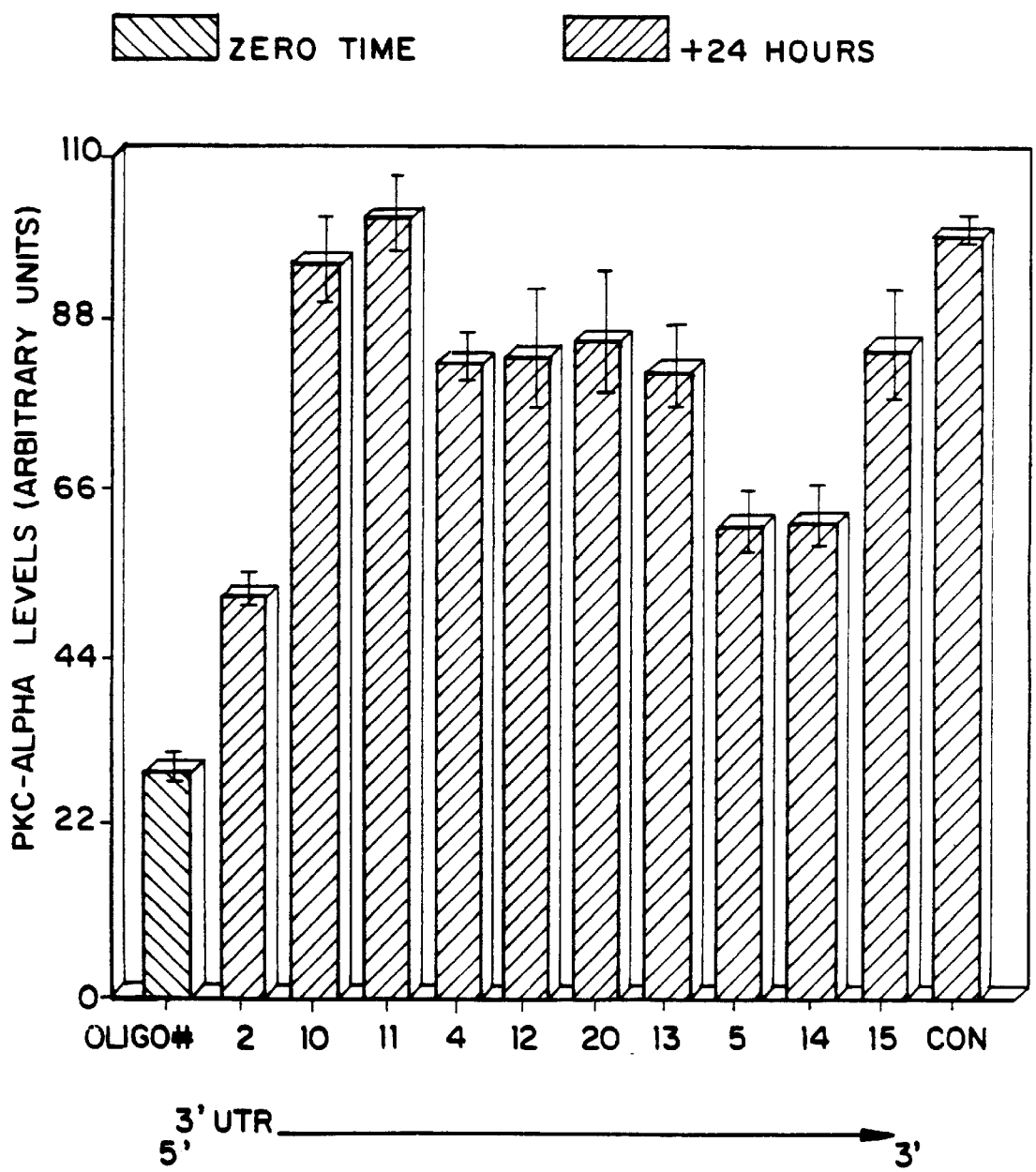

Each oligonucleotide was tested three times, in triplicate, and the results of the experiments were normalized against percentage of protein present as compared to cells which were not treated with oligonucleotide (FIGS. 1a and 1b). The five most effective oligonucleotides target the AUG start codon and regions slightly upstream and downstream from it (Sequence Nos. 1, 3, 17, 7, 6). The next most effective oligo-nucleotides are targeted toward the 3' untranslated region of the RNA (oligos 2, 5, 14).

Example 4
Other Isozymes of PKC:

Results with oligonucleotides targeting human PKC-α demonstrated that the most effective target sequences were those surrounding the translation initiation codon and the 3' untranslated region. It is believed that these sequences will also be effective targets for oligo-nucleotides directed against other isozymes of PKC. The other isozymes of human PKC for which sequence data are available are PKC-β (types I and II), PKC-γ (partial sequence) and PKC-η. Antisense oligonucleotides which are likely to be effective inhibitors of PKC are identified below. These oligonucleotides are synthesized as in Example 1, and can be screened as in Examples 2 and 3, using appropriate antibodies where available. Alternatively, a reporter gene assay system can be established, transiently co-expressing the desired isozyme of PKC with luciferase under the influence of the TPA-responsive enhancer or other suitable promoter. PKC expression is then assayed by measuring luciferase activity using standard procedures. Luciferase is extracted from cells by lysis with the detergent Triton X-100, as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY (1987). A Dynatech ML1000 luminometer is used to measure peak luminescence upon addition of luciferin (Sigma) to 625 μM. PKC-β, types I and II Sequence data are from Kubo et al., *FEBSLett.* 223: 138–142 (1987); Genbank accession numbers X06318, M27545, X07109. Sequences are numbered from the first 5' base sequenced on the cDNA. PKC-β types I and II are the result of alternative mRNA splicing of a single gene product. This results in proteins with identical amino termini (5' end of the mRNA); however, there is sequence divergence in the carboxy termini (3' end of the mRNA). The following oligonucleotides, targeted to the translation initiation codon, are expected to modulate expression of both PKC-β types I and II:

TABLE 2

OLIGONUCLEOTIDES TARGETED TO PKC-β TYPES I AND II

| SEQ ID | Sequence | Target |
|---|---|---|
| 21 | CAT CTT GCG CGC GGG GAG CC 139                                 120 | Translation init. |
| 22 | TGC GCG CGG GGA GCC GGA GC 134                                 115 | " |
| 23 | CGA GAG GTG CCG GCC CCG GG 113                                  94 | " |
| 24 | CTC TCC TCG CCC TCG CTC GG 183                                 164 | " |

The following antisense oligonucleotides are targeted to the 3'-untranslated region of PKC-β type I:

TABLE 3

OLIGONUCLEOTIDES TARGETED TO PKC-β TYPE I

| SEQ.ID | Sequence | Target |
|---|---|---|
| 25 | TGG AGT TTG CAT TCA CCT AC 2168                                2149 | 3' Untranslated |
| 26 | AAA GGC CTC TAA GAC AAG CT 2285                                2266 | " |
| 27 | GCC AGC ATG TGC ACC GTG AA 2250                                2231 | " |
| 28 | ACA CCC CAG GCT CAA CGA TG 2186                                2167 | " |
| 29 | CCG AAG CTT ACT CAC AAT TT 2569                                2550 | " |

The following antisense oligonucleotides are targeted to the 3'-untranslated region of PKC-β Type II:

TABLE 4

OLIGONUCLEOTIDES TARGETED TO PKC-β TYPE II

| SEQ.ID | Sequence | Target |
|---|---|---|
| 30 | ACT TAG CTC TTG ACT TCG GG 2160                                2141 | 3' Untranslated |
| 31 | ATG CTG CGG AAA ATA AAT TG 2420                                2401 | " |
| 32 | ATT TTA TTT TGA GCA TGT TC 2663                                2644 | " |
| 33 | TTT GGG GAT GAG GGT GAG CA 2843                                2824 | " |
| 34 | CCC ATT CCC ACA GGC CTG AG 3137                                3118 | " |

PKC-γ:

Sequence data are from Coussens et al., *Science* 233:859–866 (1986); Genbank accession number M13977. Sequences are numbered from the first 5' base sequenced in the cDNA. The full sequence is not available: the extreme 3' end of the open reading frame and the 3' untranslated region are missing. Consequently these regions are not presently available as antisense targets.

TABLE 5

OLIGONUCLEOTIDES TARGETED TO PKC-γ

| SEQ.ID | Sequence | Target |
|---|---|---|
| 35 | CGG AGC GCG CCA GGC AGG GA 51                                  32 | 5' Untranslated |
| 36 | CCT TTT CCC AGA CCA GCC AT 215                                 196 | Translation init. |

TABLE 5-continued

OLIGONUCLEOTIDES TARGETED TO PKC-γ

| SEQ.ID | Sequence | Target | |
|---|---|---|---|
| 37 | GGC CCC AGA AAC GTA GCA GG<br>195                     176 | 5' of start codon | |
| 38 | GGA TCC TGC CTT TCT TGG GG<br>170                     151 | 5' Untranslated | |
| 39 | CAG CCA TGG CCC CAG AAA CG<br>202                     183 | Translation init. | |

PKC-η:

Sequence data for PKC-η are from Bacher and colleagues [Bacher et al., *Mol. Cell. Biol.* 11:26–133 (1991)]; Genbank accession number M55284. They assign their isozyme the name PKC-L; however the sequence is almost identical to that of mouse PKC-η, so the latter nomenclature is used here for consistency. Sequences are numbered from the first 5' base sequenced in the cDNA.

TABLE 6

OLIGONUCLEOTIDES TARGETED TO PKC-η

| SEQ.ID | Sequence | Target | |
|---|---|---|---|
| 40 | CGA CAT GCC GGC GCC GCT GC<br>172                     153 | Translation init. | |
| 41 | CAG ACG ACA TGC CGG CGC CG<br>176                     157 | " | |
| 42 | GCC TGC TTC GCA GCG GGA GA<br>138                     119 | " | |
| 43 | ACA GGT GCA GGA GTC GAG GC<br>86                      67 | " | |
| 44 | GTC CCG TCT CAG GCC AGC CC<br>111                     92 | " | |
| 45 | CCT CAC CGA TGC GGA CCC TC<br>221                     202 | " | |
| 46 | ATT GAA CTT CAT GGT GCC AG<br>193                     174 | " | |
| 47 | TCT CAC TCC CCA TAA GGC TA<br>2046                    2027 | 3' Untranslated | |
| 48 | TTC CTT TGG GTT CTC GTG CC<br>2067                    2048 | " | |
| 49 | TTC CAT CCT TCG ACA GAG TT<br>2353                    2336 | " | |
| 50 | AGG CTG ATG CTG GGA AGG TC<br>2300                    2281 | " | |
| 51 | GTT CTA AGG CTG ATG CTG GG<br>2306                    2287 | " | |

Figure 2:
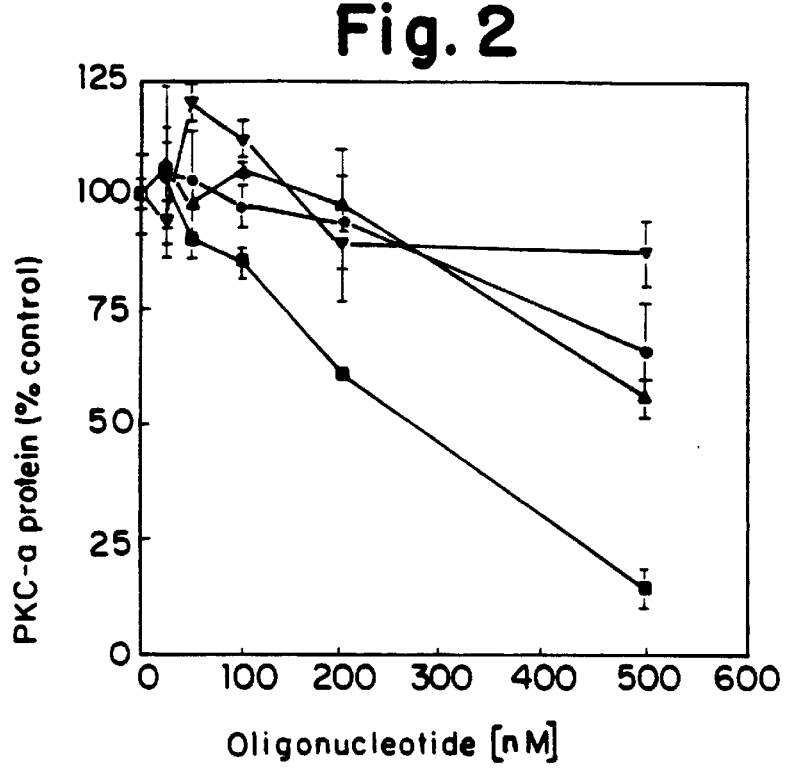
FIG. 2 is a line graph showing dose-dependent reduction of PKC-α protein levels after oligonucleotide treatment of A549 cells. ▼=ISIS 4632; ■=ISIS 4649; "=ISIS 4636; ▲=ISIS 4648.

Example 5
Dose Response of Phosphorothioate/2'-O-methyl Oligonucleotide Effects on PKC-α Protein Synthesis:

A series of phosphorothioate, fully 2'-O-methyl oligonucleotides having SEQ ID NO: 1, 2, 3 and 5 were synthesized. A549 cells were treated with 500 nM PDBu for 18 hours to downregulate PKC-α synthesis, washed to remove PDBu and then treated with oligonucleotide and DOTMA/DOPE cationic liposomes. Medium was replaced after four hours and the cells were allowed to recover for another 20 hours. Proteins were extracted and PKC-α protein levels were determined by immunoblotting as described in Example 3. Results were quantified with a phosphorimager (Molecular Dynamics, Sunnyvale Calif.) and are shown in FIG. 2 expressed as percent of control (saline treatment). ISIS 4649 (SEQ ID NO: 3; squares) reduced PKC-α protein levels by 85–90% at 500 nM and had an IC50 of approximately 260 nM.

Figure 3:
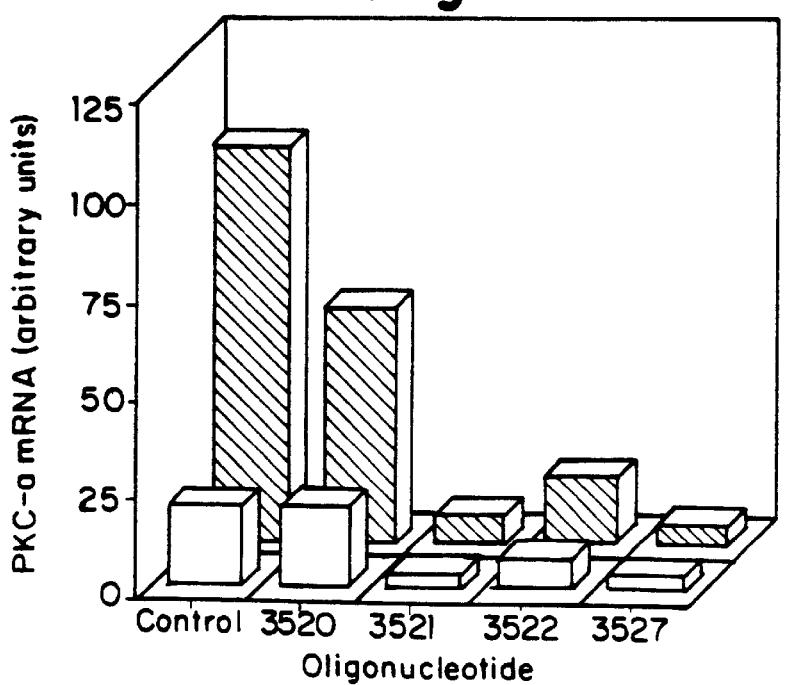
FIG. 3 is a bar graph showing reduction of PKC-α mRNA after treatment of A549 cells with oligonucleotides. Hatched bars represent the 8.5 kb transcript, plain bars represent the 4.0 kb transcript.

Example 6
Effect of Antisense Oligonucleotides on PKC-α mRNA Levels:

A549 cells were treated with phosphorothioate oligonucleotides at 500 nM for four hours in the presence of the cationic lipids DOTMA/DOPE, washed and allowed to recover for an additional 20 hours. Total RNA was extracted and 20 μg of each was resolved on 1.2% gels and transferred to nylon membranes. These blots were probed with a $^{32}$P radiolabeled PKC-α cDNA probe and then stripped and reprobed with a radiolabeled G3PDH probe to confirm equal RNA loading. Each oligonucleotide (3520, 3521, 3522 and 3527) was used in duplicate. The two major PKC-α transcripts (8.5 kb and 4.0 kb) were examined and quantified with a PhosphorImager (Molecular Dynamics, Sunnyvale Calif.). Results are shown in FIG. 3. Oligonucleotides 3521 (SEQ ID NO: 2), 3522 (SEQ ID NO: 3) and 3527 (SEQ ID NO: 5) gave better than 50% reduction of PKC-α mRNA levels. Oligonucleotides 3521 and 3527 gave approximately 80% reduction of the smaller transcript and over 90% reduction of the larger transcript.

Figure 4:
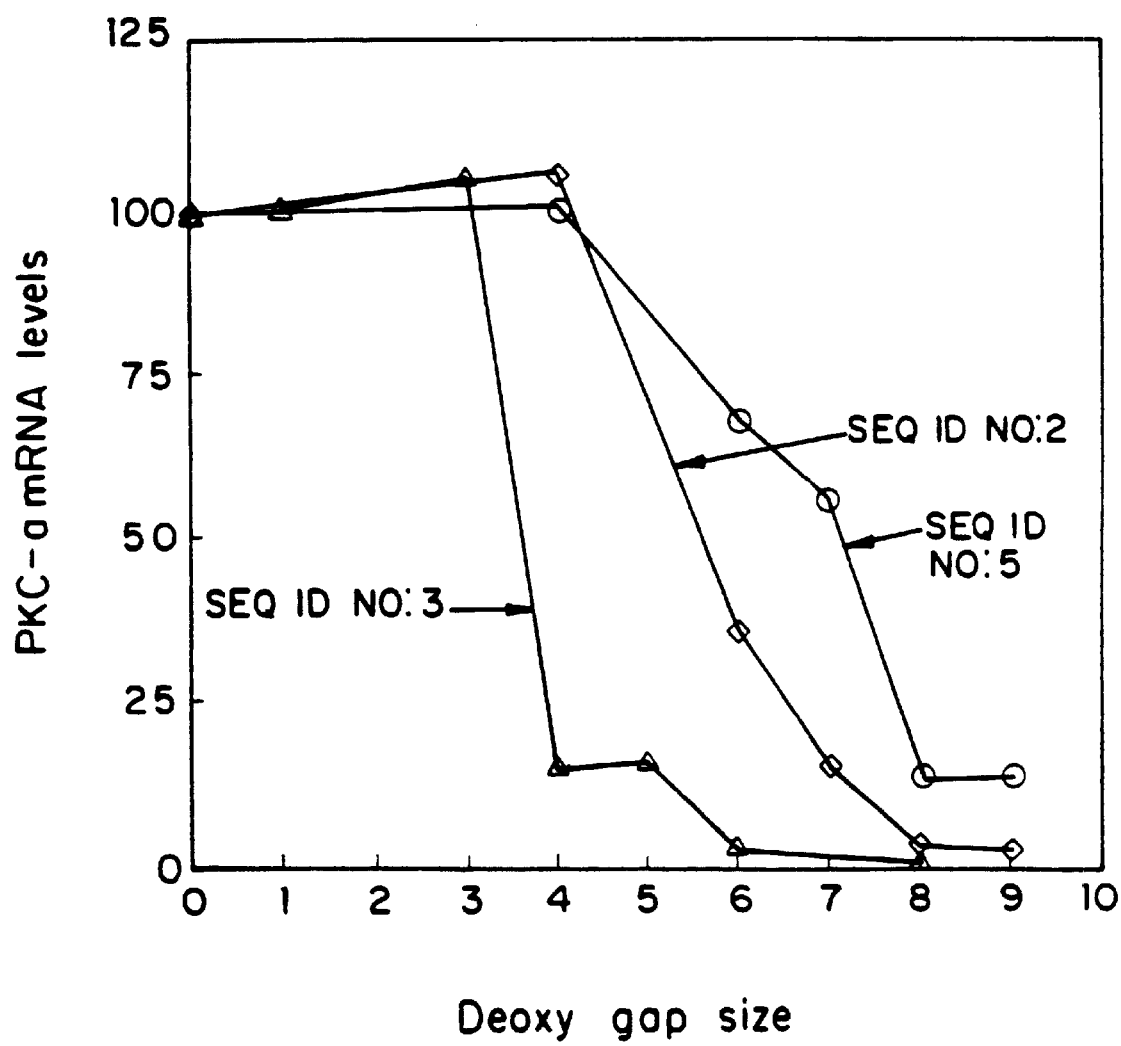
FIG. 4 is a line graph showing the relationship between deoxy gap length and activity of chimeric oligonucleotides against PKC.

Example 7
Chimeric (Deoxy Gapped) 2'-O-methyl Oligonucleotides:

Oligonucleotides 3521 (SEQ ID NO: 2), 3522 (SEQ ID NO: 3) and 3527 (SEQ ID NO: 5) were chosen for further study and modification. Oligonucleotides having these sequences were synthesized as uniformly phosphorothioate chimeric oligonucleotides having a centered deoxy gap of various lengths flanked by 2'-O-methylated regions. These oligonucleotides (500 nM concentration) were tested for effects on PKC-α mRNA levels by Northern blot analysis. Results are shown in FIG. 4. Deoxy gaps of eight nucleotides or more gave maximal reduction of PKC-α mRNA levels (both transcripts) in all cases. The oligo-nucleotide having SEQ ID NO: 3 reduced PKC-α mRNA by approximately 83% with a deoxy gap length of four nucleotides, and gave nearly complete reduction of PKC-α mRNA with a deoxy gap length of six or more.

Figure 5:
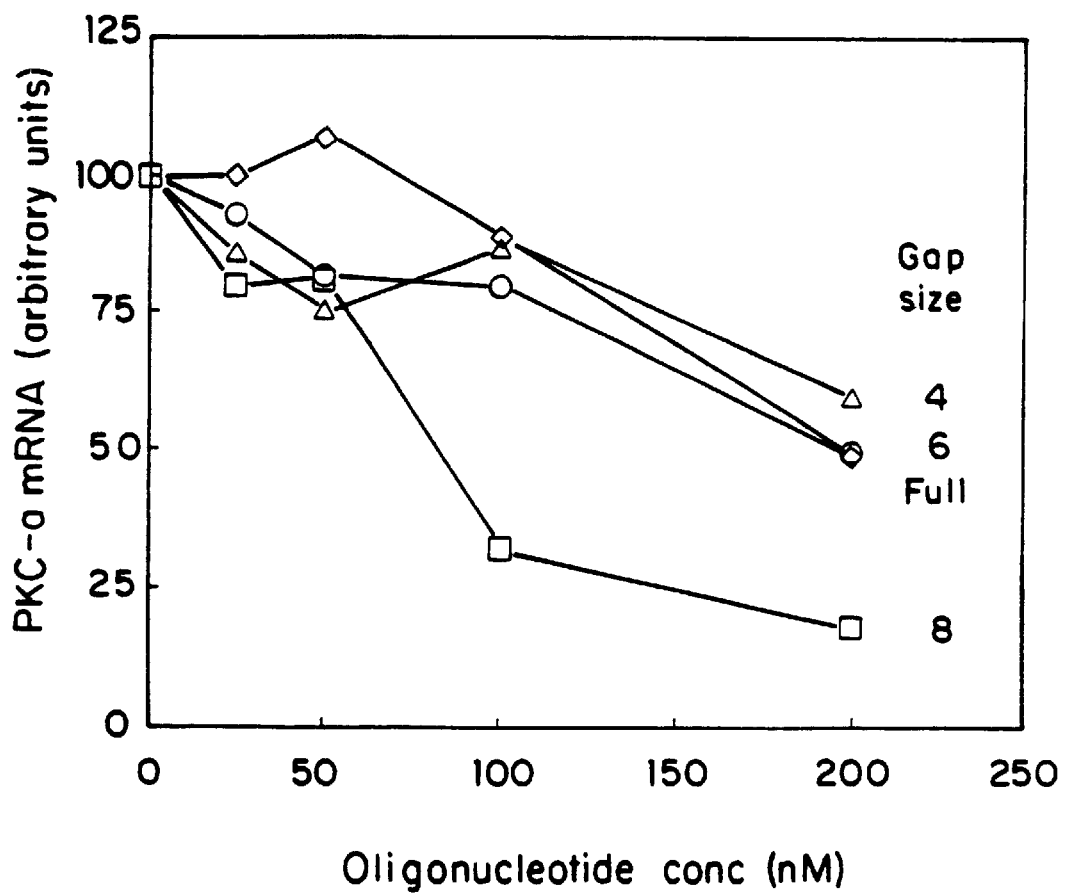
FIG. 5 is a line graph showing dose response curves for chimeric oligonucleotides (all SEQ ID NO: 3) with different deoxy gap lengths.

Dose-response curves for these oligonucleotides are shown in FIG. 5. The 2'-O-methyl chimeric oligonucleotides with four- or six-nucleotide deoxy gaps have an IC50 for PKC-α mRNA reduction (concentration of oligonucleotide needed to give a 50% reduction in PKC-α mRNA levels) of 200–250 nM, as did the full-deoxy oligonucleotide (all are phosphorothioates throughout). The 2'-O-methyl chimeric oligonucleotide with an 8-nucleotide deoxy gap had an IC50 of approximately 85 nM.

Several variations of this chimeric oligonucleotide (SEQ. ID NO: 3) were compared for ability to lower PKC-α mRNA levels. These oligonucleotides are shown in Table 7.

TABLE 7

Chimeric 2'-O-methyl/deoxy P=S oligonucleotides
bold = 2'-O-methyl; s = P=S linkage,
o = P=O linkage

| OLIGO # | SEQUENCE | SEQ ID NO: |
|---|---|---|
| 3522 | AsAsAsAsCsGsTsCsAsGsCsCsAsTsGsGsTsCsCsC | 3 |
| 5352 | AsAsAsAsCsGsTsCsAsGsCsCsAsTsGsGsTsCsCsC | 3 |
| 6996 | AoAoAoAoCoGsTsCsAsGsCsCsAsTsGoGoToCoCoC | 3 |
| 7008 | AsAoAoAoCoGsTsCsAsGsCsCSAsTsGoGoToCoCsC | 3 |
| 7024 | AsAoAoAoCoGsToCsAoGsCoCsAsTsGoGoToCoCsC | 3 |

Figure 6:
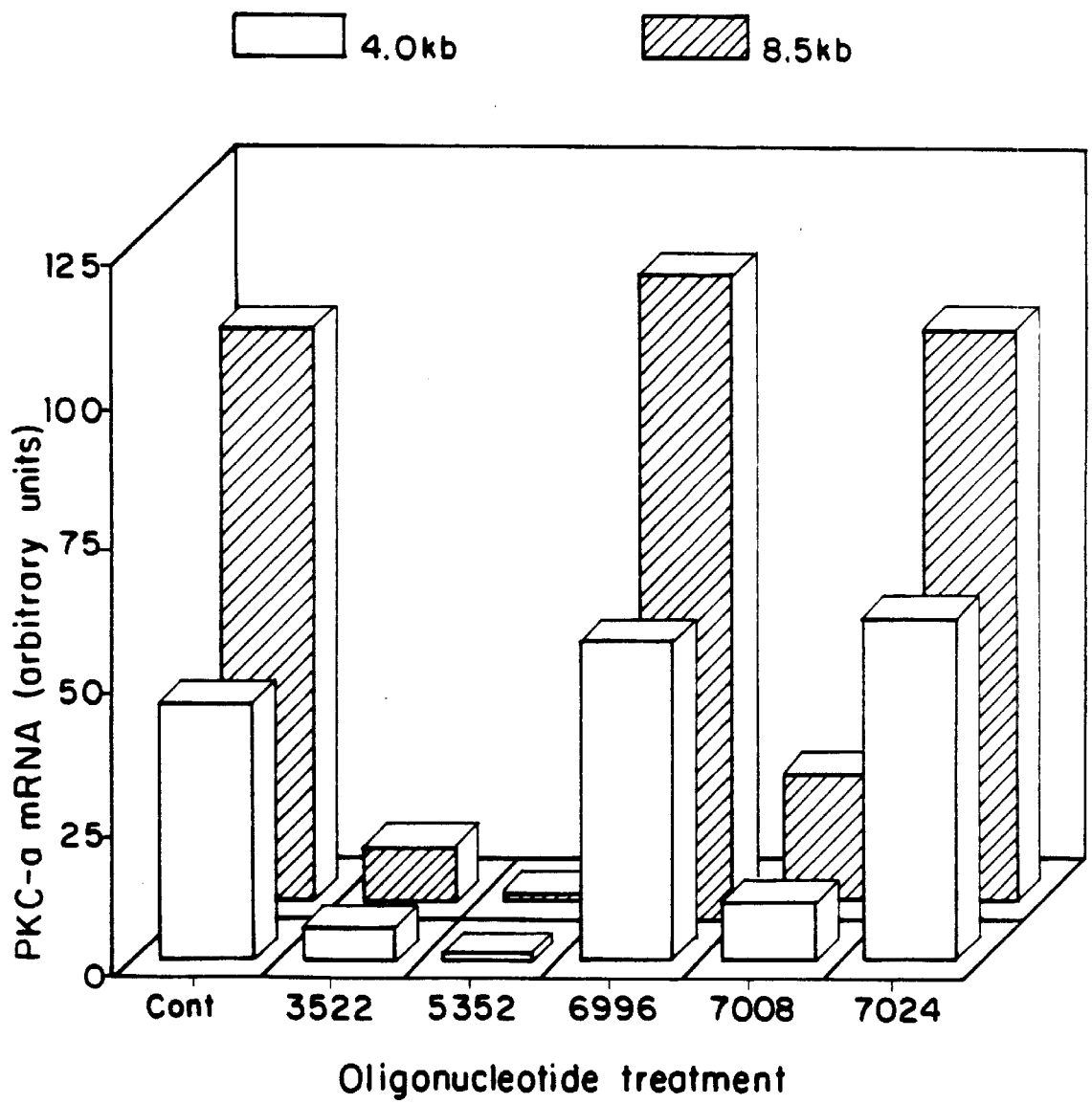
FIG. 6 is a bar graph showing the effects of several 2'-O-methyl chimeric oligonucleotides of SEQ ID NO: 3 on PKC-α mRNA levels. Hatched bars represent the 8.5 kb transcript, plain bars represent the 4.0 kb transcript.

Effects of these oligonucleotides on PKC-α mRNA levels is shown in FIG. 6. Oligonucleotides 7008, 3522 and 5352 show reduction of PKC-α mRNA, with 5352 being most active.

A series of 2'-O-propyl chimeric oligonucleotides was synthesized having SEQ ID NO: 3. These oligonucleotides are shown in Table 8.

TABLE 8

Chimeric 2'-O-propyl/deoxy P=S oligonucleotides
bold = 2'-O-propyl; s = P=S linkage,
o = P=O linkage

| OLIGO # | SEQUENCE | SEQ ID NO: |
|---|---|---|
| 7199 | AsAsAsAsCsGsTsCsAsGsCsCsAsTsGsGsTsCsCsC | 3 |
| 7273 | AoAoAoAoCoGsTsCsAsGsCsCsAsTsGoGoToCoCoC | 3 |
| 7294 | AsAoAoAoCoGsTsCsAsGsCsCsAsTsGoGoToCoCsC | 3 |
| 7295 | AsAoAoAoCoGsToCsAoGsCoCsAsTsGoGoToCoCsC | 3 |

Figure 7:
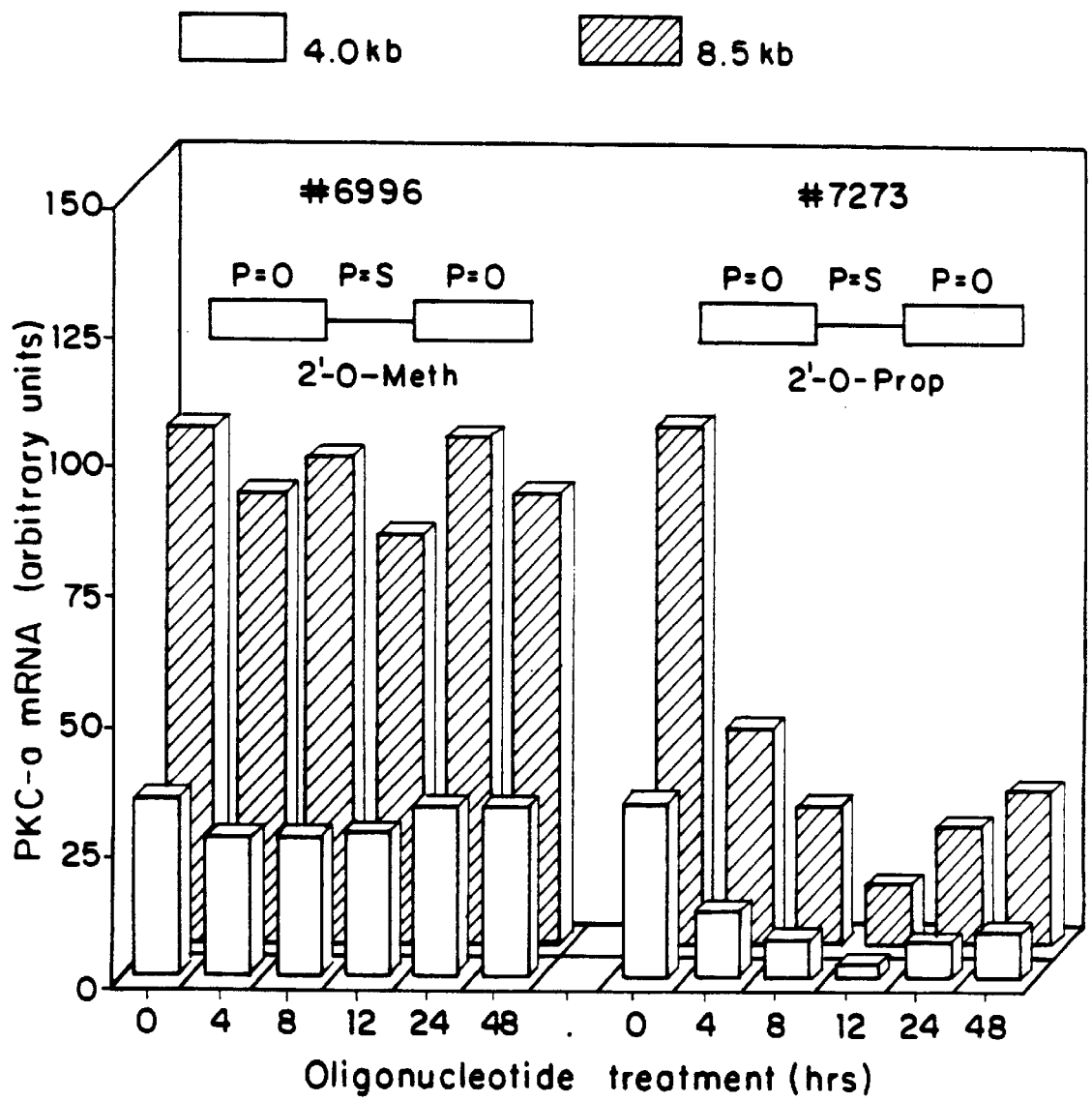
FIG. 7 is a bar graph and diagram showing the effects of several 2'-O-methyl and 2'-O-propyl chimeric oligonucleotides (6996, 7273) of SEQ ID NO: 3 on PKC-α mRNA levels. Hatched bars represent the 8.5 kb transcript, plain bars represent the 4.0 kb transcript.
Figure 8:
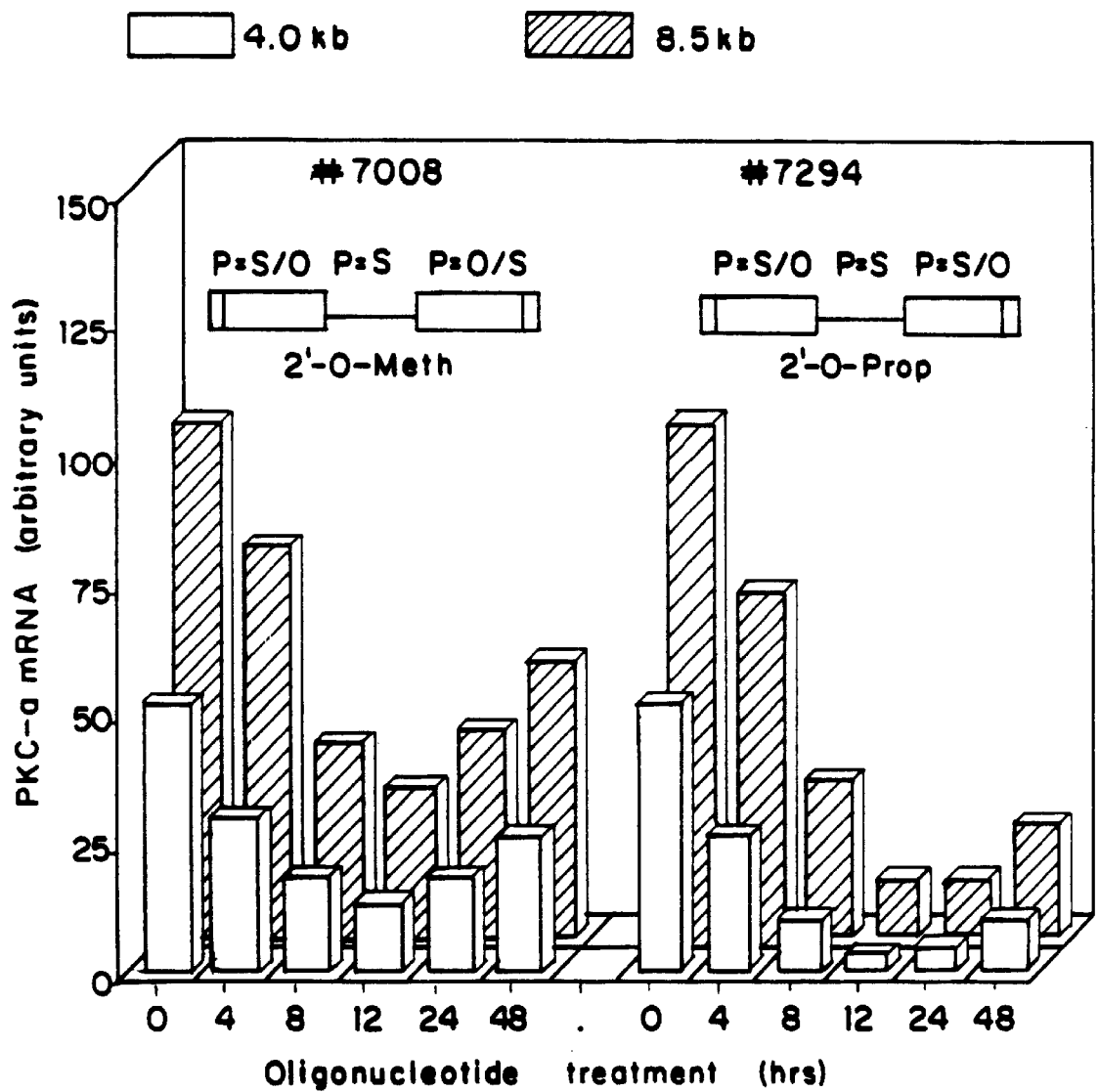
FIG. 8 is a bar graph and diagram showing the effects of additional 2'-O-methyl and 2'-O-propyl chimeric oligonucleotides (7008, 7294) of SEQ ID NO: 3 on PKC-α mRNA levels. Hatched bars represent the 8.5 kb transcript, plain bars represent the 4.0 kb transcript.

These 2'-O-propyl chimeric oligonucleotides were compared to the 2'-O-methyl chimeric oligonucleotides. Oligonucleotides 7273 and 7294 were more active than their 2'-O-methyl counterparts at lowering PKC-α mRNA levels. This is shown in FIGS. 7 and 8.

Example 8
Additional Oligonucleotides Which Decrease PKC-α mRNA:

Additional phosphorothioate oligonucleotides targeted to the human PKC-α 3' untranslated region were designed and synthesized. These sequences are shown in Table 9.

TABLE 9

Chimeric 2'-O-propyl/deoxy P=S oligonucleotides
targeted to PKC-α 3' UTR
bold = 2'-O-propyl; s = P=S linkage,
o = P=O linkage

| OLIGO # | SEQUENCE | SEQ ID NO: |
|---|---|---|
| 6632 | TsTsCs TsCsGs CsTsGs GsTsGs AsGsTs TsTsC | 52 |
| 6653 | TsTsCs TsCsGs CsTsGs GsTsGs AsGsTs TsTsC | 52 |
| 6665 | ToToCo TsCsGs CsTsGs GsTsGs AsGsTo ToToC | 52 |
| 7082 | TsCsTs CsGsCs TsGsGs TsGsAs GsTsTs TsC | 53 |
| 7083 | TsCsTs CsGsCs TsGsGs TsGsAs GsTsTs TsC | 53 |
| 7084 | ToCoTo CsGsCs TsGsGs TsGsAs GsToTo ToC | 53 |

Figure 9A:
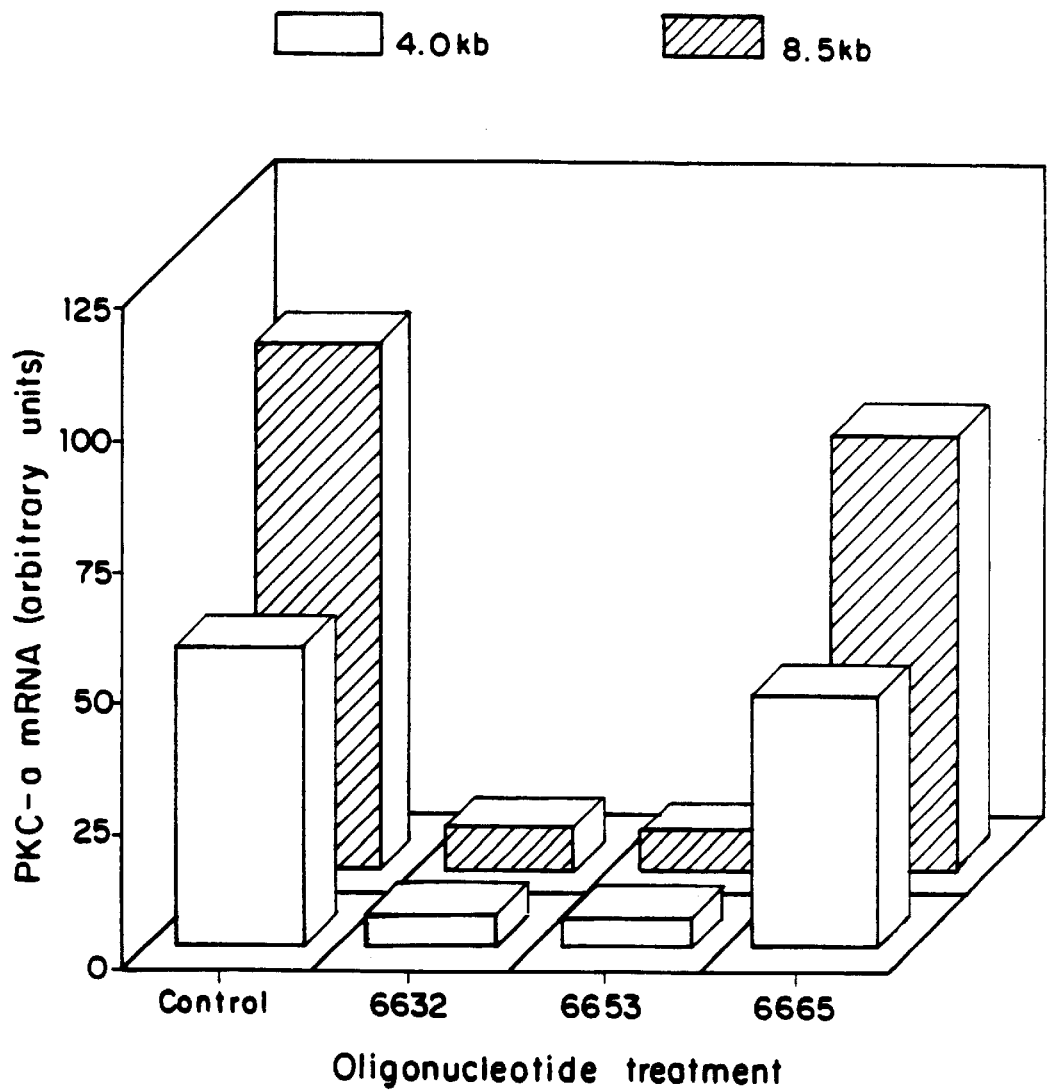
FIG. 9A shows oligonucleotides 6632, 6653 and 6665.
Figure 9B:
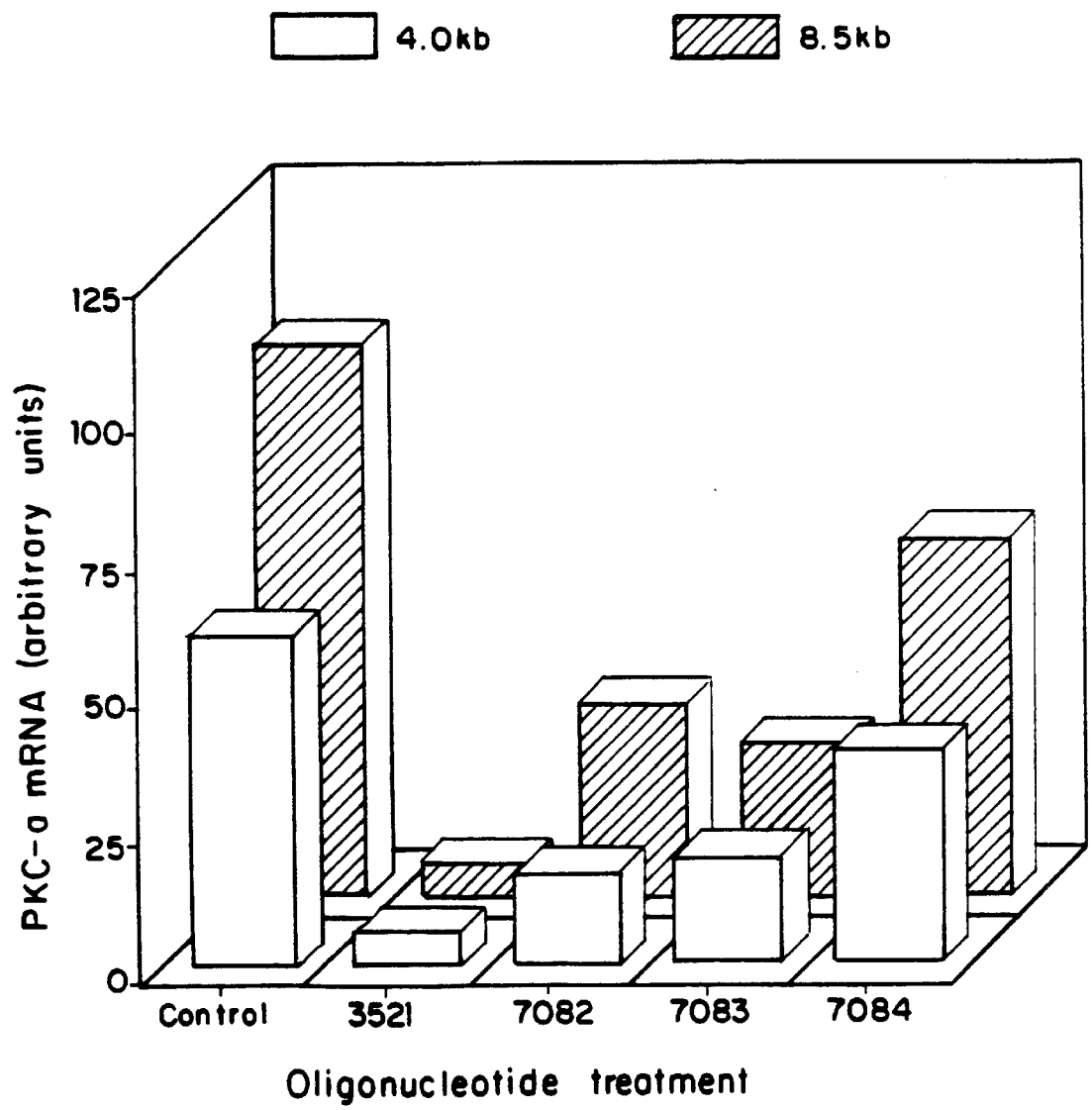
FIG. 9B shows oligonucleotides 3521 (for comparison), 7082, 7083 and 7084. Hatched bars represent the 8.5 kb transcript, plain bars represent the 4.0 kb transcript.

As shown in FIG. 9, oligonucleotides 6632, 6653, 7082 and 7083 are most active in reducing PKC-α mRNA levels.

Example 9
Culture of Human A549 Lung Tumor Cells:

The human lung carcinoma cell line A549 was obtained from the American Type Culture Collection (Bethesda Md.). Cells were grown in Dulbecco's Modified Eagle's Medium (Irvine Scientific, Irvine Calif.) containing 1 gm glucose/liter and 10% fetal calf serum (Irvine Scientific). Cells were trypsinized and washed and resuspended in the same medium for introduction into mice.

Example 10
Effect of ISIS 3521 on the Growth of Human A549 Lung Tumor Cells in Nude Mice:

200 μl of A549 cells (5×10$^6$ cells) were implanted subcutaneously in the inner thigh of nude mice. ISIS 3521, a phosphorothioate oligonucleotide with Sequence ID NO 2 was administered twice weekly for four weeks, beginning one week following tumor cell inoculation. Oligonucleotides were formulated with cationic lipids (DMRIE/DOPE) and given subcutaneously in the vicinity of the tumor. Oligonucleotide dosage was 5 mg/kg with 60 mg/kg cationic lipid. Tumor size was recorded weekly.

Figure 10:
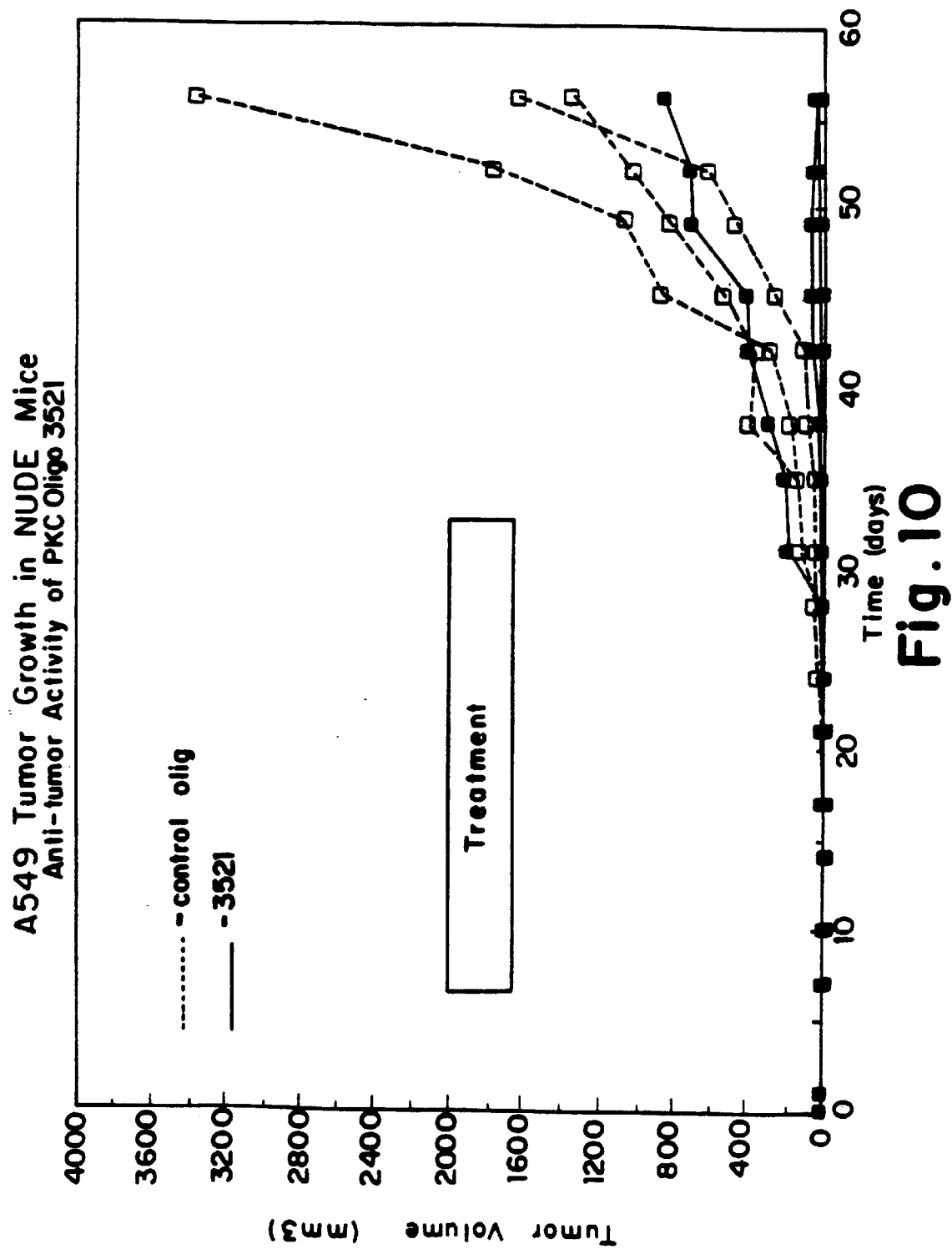
FIG. 10 is a line graph showing anti-tumor activity of ISIS 3521. Each dashed line represents tumor volume in one animal treated with control oligonucleotide; each solid line represents tumor volume in one animal treated with ISIS 3521.

As shown in FIG. 10, tumor growth was almost completely inhibited in two of the three mice, and reduced compared to control in the third mouse. This inhibition of tumor growth by ISIS 3521 is statistically significant. The control oligonucleotide (ISIS 1082) is a 21-mer phosphorothioate oligonucleotide without significant sequence homology to the PKC mRNA target.

Administration of oligonucleotides to mice whose tumors had already reached detectable size had no discernable effect on subsequent tumor growth.

Figure 11A:
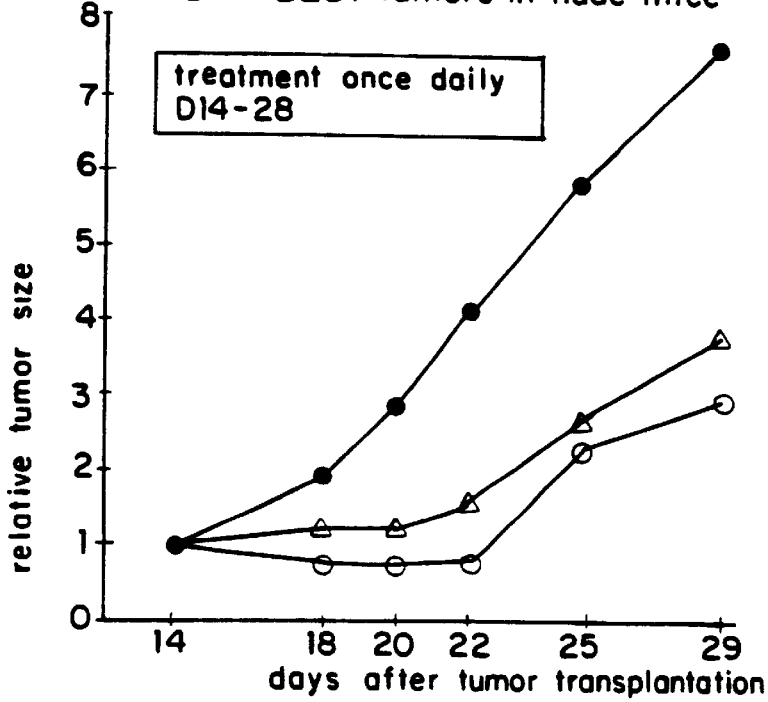
FIG. 11A shows results obtained with ISIS 3521.
Figure 11B:
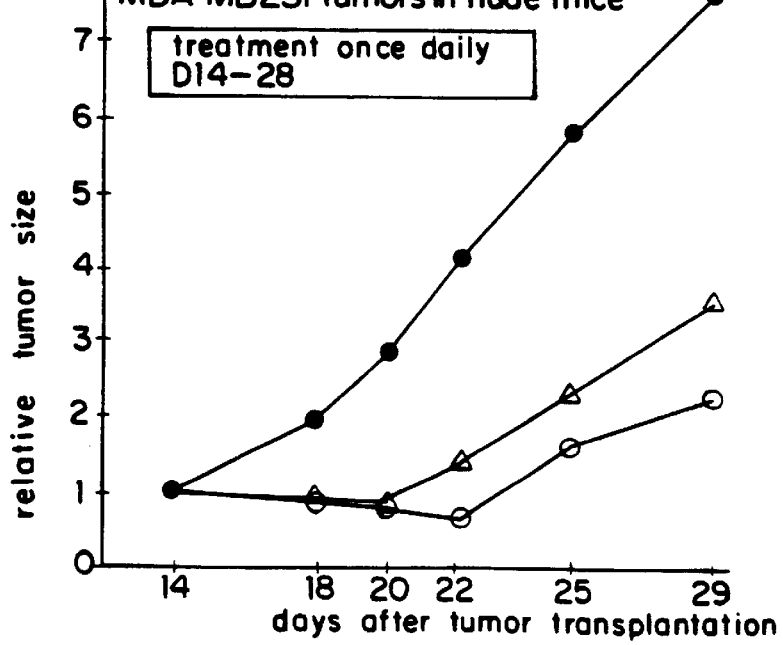
FIG. 11B shows results obtained with ISIS 3527. Each line represents tumor volume in one animal "=control; ○=oligonucleotide at 60 mg/kg; Δ=oligonucleotide at 6 mg/kg.

Example 11
Effect of Antisense Oligonucleotides on Growth of Human MDA-MB231 Tumors in Nude Mice:

MDA-MB231 human breast carcinoma cells were obtained from the American Type Culture Collection (Bethesda, Md.). Serially transplanted MDA-MB231 tumors were established subcutaneously in nude mice. Beginning two weeks later, oligonucleotides 3521 and 3527, a phosphorothioate oligonucleotide having Sequence ID NO. 5, in saline, were administered intravenously daily for 14 days at dosages of 60 mg/kg and 6 mg/kg. Control oligonucleotide ISIS 1082 was also administered at these doses, and a saline control was also given. Tumor growth rates were monitored for the two-week period of oligonucleotide administration. As shown in FIG. 11, both PKC-α oligonucleotides (3521 and 3527) significantly inhibit tumor growth at dosages of 60 mg/kg and 6 mg/kg. The control oligonucleotide (ISIS 1082) also showed some reduction in tumor growth, but this effect was less than with antisense oligonucleotides even at high doses, and considerably less at the lower dose. A lower-dose study was conducted using the same oligonucleotides at 6 mg/kg and 0.6 mg/kg. At 0.6 mg/kg ISIS 3521 significantly reduced tumor growth. At this concentration, ISIS 3527 also reduced tumor growth, but this result was not statistically significant.

Example 12
Effect of Oligonucleotides on the Growth of Murine Lewis Lung Carcinoma in Mice:

Serially transplanted murine Lewis lung carcinomas were established in mice. Oligonucleotides 3521 and 3527 were administered intravenously every day for 14 days at doses of 6 mg/kg and 0.6 mg/kg. Tumor growth rates were monitored for the two-week period of oligonucleotide administration. As expected, these oligonucleotides, which are targeted to human PKC sequences, had insignificant effects on the mouse-derived tumors.

Example 13
Effects of Antisense Oligonucleotide ISIS 4189 on Endogenous PKC-α Expression in Hairless Mice:

In order to study oligonucleotide effects on endogenous PKC mRNA levels in normal animals, it was necessary to employ an oligonucleotide complementary to the murine PKC-α. ISIS 4189 is a 20-mer phosphorothioate oligonucleotide targeted to the AUG codon of mouse PKC-α. This region is without homology to the human PKC sequence and the oligonucleotide has no effect on expression of PKC-α in human cells. ISIS 4189 has an IC50 of 200 nM for mRNA reduction in C127 mouse breast epithelial cells. ISIS 4189 in saline was administered intraperitoneally to hairless mice at concentrations of 1, 10 or 100 mg/kg body weight. Injections were given daily for seven days. Tissues from liver, kidney, spleen, lung and skin were removed and PKC-α mRNA and protein levels were determined. Histopathological examination was also performed on liver, kidney and lung samples. ISIS 4189 at 100 mg/kg inhibited endogenous PKC-α mRNA levels in the mouse liver to 10–15% of control (saline) levels.

Example 14
Screening of Antisense Oligonucleotides Targeted to Human PKC-η:

A series of 20-mer phosphorothioate oligonucleotides complementary to human PKC-η were synthesized. These oligonucleotides were screened at a concentration of 500 nM for ability to decrease PKC-η mRNA levels in human A549 cells, using a Northern blot assay. The oligonucleotide sequences are shown in Table 10 and the results are shown in FIG. 12.

TABLE 10

OLIGONUCLEOTIDES TARGETED TO HUMAN PKC-η mRNA

| SEQ ID | Sequence | Target | ISIS # |
|---|---|---|---|
| 6431 | CGA CAT GCC GGC GCC GCT GC | AUG | 40 |
| 6442 | CAG ACG ACA TGC CGG CGC CG | AUG | 41 |
| 6443 | GCC TGC TTC GCA GCG GGA GA | 5'UTR | 42 |
| 6432 | ACA GGT GCA GGA GTC GAG GC | 5'UTR | 43 |
| 6433 | GTC CCG TCT CAG GCC AGC CC | 5'UTR | 44 |
| 6435 | CCT CAC CGA TGC GGA CCC TC | Coding | 45 |
| 6441 | ATT GAA CTT CAT GGT GCC AG | Coding | 46 |
| 6581 | TCT CAC TCC CCA TAA GGC TA | 3'UTR | 47 |
| 6580 | TTC CTT TGG GTT CTC GTG CC | 3'UTR | 48 |
| 6436 | AAC TCG AGG TGG CCG CCG TC | Coding | 54 |
| 6434 | CGC CTT CGC ATA GCC CTT TG | Coding | 55 |
| 6444 | GGA AGG GGT GAT TGC GGG CC | Coding | 56 |
| 6445 | AAC ACG CCC ATT GCC CAC CA | Coding | 57 |
| 6446 | GTC TCA AGA TGG CGT GCT CG | Coding | 58 |
| 6553 | GCG ATG GTT CAG CTG GGC CC | Coding | 59 |
| 6605 | GCC CTC TCT CTC ACT CCC CA | 3'UTR | 60 |
| 6579 | CTG GGA AGG TCC GAT AGA GG | 3'UTR | 61 |
| 6603 | AAG GCT GAT GCT GGG AAG GT | 3'UTR | 62 |

Oligonucleotides 6432, 6443, 6431, 6442, 6435, 6434, 6445, 6553, 6581 and 6603 reduced PKC-η mRNA levels by greater than 50%. The most potent oligonucleotides were ISIS 6581 (targeting 3' untranslated region) and ISIS 6445 (targeting coding region) which gave nearly complete loss of PKC mRNA in this assay.

Example 15
Screening of Antisense Oligonucleotides Targeted to PKC-δ:

A series of 20-mer phosphorothioate oligonucleotides complementary to human PKC-δ were synthesized. These oligonucleotides were screened by Northern blot assay at a concentration of 500 nM for their ability to decrease PKC-δ mRNA levels in human A549 cells. The oligonucleotide sequences and the results, expressed as percent inhibition of PKC-δ mRNA expression, are shown in Table 11.

TABLE 11

Antisense oligonucleotides targeted to PKC-δ

| Isis # | Site | Sequence | % Inhib | SEQ ID: |
|---|---|---|---|---|
| 10299 | AUG | GCA GGA ACG GCG CCA TGG TG | 0% | 63 |
| 10300 | Coding | CTG GTT CGC CTC GTC CTC GG | 25 | 64 |
| 10301 | Coding | ATC TGG ATG ACG CGC CCC TC | 26 | 65 |
| 10302 | Coding | TTC TTG CAG CGC TCG GCC AG | 8 | 66 |
| 10303 | Coding | TGC AAT CCA CGT CCT CCA GG | 50 | 67 |
| 10304 | Coding | GGC TCC GCG GCG GTT CAT CG | 12 | 68 |

TABLE 11-continued

Antisense oligonucleotides targeted to PKC-δ

| Isis # | Site | Sequence | % Inhib | SEQ ID: |
|---|---|---|---|---|
| 10305 | Coding | AAG CGG TGC GGC ATG TCG AT | 43 | 69 |
| 10306 | Coding | GCA GGC TGC CGC AGT GGT CA | 12 | 70 |
| 10307 | Coding | CCT CCC CAG CAA CTC CGG TC | 36 | 71 |
| 10308 | Coding | AGC GGC CTT TGT CCT GGA TG | 11 | 72 |
| 10309 | Coding | GGC CAT CCC GGT CCA ACA GC | 43 | 73 |
| 10310 | Coding | GGT GCT GGC CCG GCT CTC CC | 66 | 74 |
| 10311 | Coding | GGA CCC CGA AAG ACC ACC AG | 77 | 75 |
| 10312 | Coding | GTG GCT CCA ACC TCC GCT TT | 18 | 76 |
| 10313 | Coding | AGG AGG TGC TCG AAT TTG GG | 0% | 77 |

Oligonucleotides ISIS 10303, ISIS 10310 and ISIS 10311 gave at least 50% inhibition of PKC-67 mRNA expression in this assay and are preferred.

Example 16
Screening of Antisense Oligonucleotides Targeted to PKC-ε:

A series of 20-mer phosphorothioate oligonucleotides complementary to human PKC-ε were synthesized. These oligonucleotides were screened by Northern blot assay at a concentration of 500 nM for their ability to decrease PKC-ε mRNA levels in human A549 cells. The oligonucleotide sequences and the results, expressed as percent inhibition of PKC-ε mRNA expression, are shown in Table 12.

TABLE 12

Antisense oligonucleotides targeted to PKC-ε

| Isis # | Site | Sequence | % Inhib | SEQ ID: |
|---|---|---|---|---|
| 7933 | AUG | ACT ACC ATG GTC GGG GCG GG | 0% | 78 |
| 7934 | Coding | GTC CCA CCG CAT GGC GCA GC | 0 | 79 |
| 7935 | Coding | GTT TGG CCG ATG CGC GAG TC | 0 | 80 |
| 7936 | Coding | TGC AGT TGG CCA CGA AGT CG | 0 | 81 |
| 8032 | Coding | GTG GGG CAT GTT GAC GCT GA | 0 | 82 |
| 8031 | Coding | CCA GAG CAG GGA CCC ACA GT | 0 | 83 |
| 7939 | Coding | TCT CCT CGG TTG TCA AAT GA | 0 | 84 |
| 7940 | Coding | CGG TGC TCC TCT CCT CGG TT | 0 | 85 |
| 7941 | Coding | AGC CAA AAT CCT CTT CTC TG | 0 | 86 |
| 7942 | Coding | CAT GAG GGC CGA TGT GAC CT | 67 | 87 |
| 7943 | Coding | ATC CCT TCC TTG CAC ATC CC | 3 | 88 |
| 7944 | Coding | CCC CAG GGC CCA CCA GTC CA | 38 | 89 |
| 7945 | Coding | AGC ACC CCC AGG GCC CAC CA | 42 | 90 |
| 7946 | Coding | CGT ACA TCA GCA CCC CCA GG | 42 | 91 |
| 7947 | Coding | CCA GCC ATC ATC TCG TAC AT | 9 | 92 |
| 7948 | Coding | TGC CAC ACA GCC CAG GCG CA | 55 | 93 |
| 7949 | Stop | TCA GGG CAT CAG GTC TTC AC | 0 | 94 |
| 7950 | Stop | CTC TCA GGG CAT CAG GTC TT | 0 | 95 |

Oligonucleotides ISIS 7942 and ISIS 7948 gave at least 50% inhibition of PKC-68 mRNA expression in this assay and are preferred.

Additional oligonucleotides targeted to PKC-ε were synthesized. These are shown in Table 13.

TABLE 13

Antisense oligonucleotides targeted to PKC-ε

| Isis # | Site | Sequence | SEQ ID: |
|---|---|---|---|
| A | Coding | AAG GAA AGT CTG CGG CCG GG | 96 |
| B | Coding | TGG CGG CTC CCG TTC TGC AG | 97 |
| C | Coding | GCT TCC TCG GCC GCA TGC GT | 98 |
| D | Coding | TTG ACG CTG AAC CGC TGG GA | 99 |
| E | Coding | GCC CGG TGC TCC TCT CCT CG | 100 |

TABLE 13-continued

Antisense oligonucleotides targeted to PKC-ε

| Isis # | Site | Sequence | SEQ ID: |
|---|---|---|---|
| F | Coding | GGG CCG ATG TGA CCT CTG CA | 101 |
| G | Coding | TGG AGG AAC ATG AGG GCC GA | 102 |
| H | Coding | CCC CCA GGG CCC ACC AGT CC | 103 |
| I | Coding | TGC GAT GCC ACA CAG CCC AG | 104 |
| J | Stop | TGG GCT CTC AGG GCA TCA GG | 105 |

Example 17

Screening of Antisense Oligonucleotides Targeted to PKC-ζ:

A series of 20-mer phosphorothioate oligonucleotides complementary to human PKC-ζ were synthesized. These oligonucleotides were screened by Northern blot assay at a concentration of 500 nM for their ability to decrease PKC-ζ mRNA levels in human A549 cells. The oligonucleotide sequences and the results, expressed as percent inhibition of PKC-ζ mRNA expression, are shown in Table 14.

TABLE 14

Antisense oligonucleotides targeted to PKC-ζ

| Isis # | Site | Sequence | % Inhib | SEQ ID: |
|---|---|---|---|---|
| 9007 | AUG | CGC CGC TCC CTT CCA TCT TG | 67% | 106 |
| 9008 | Coding | CCC CGT AAT GCG CCT TGA GG | 64 | 107 |
| 9009 | Coding | CTG TCC ACC CAC TTG AGG GT | 14 | 108 |
| 9012 | Coding | TTG GAA GAG GTG GCC GTT GG | 78 | 109 |
| 9013 | Coding | CCT GTT AAA GCG CTT GGC TT | 67 | 110 |
| 9014 | Coding | TGC AGG TCA GCG GGA CGA GG | 40 | 111 |
| 9016 | Coding | AGC CCC TGA GAG ATT TTG AT | 0 | 112 |
| 9017 | Coding | TTC TTC AAC CGC ACC AGG AG | 67 | 113 |
| 9019 | Coding | TCC TTG CAC ATG CCG TAG TC | 24 | 114 |
| 9021 | Coding | GGA GCG CCC GGC CAT CAT CT | 78 | 115 |
| 9022 | Coding | GGG CTC GCT GGT GAA CTG TG | 85 | 116 |
| 9023 | 3'UTR | GAC GCA CGC GGC CTC ACA CC | 88 | 117 |
| 9025 | 3'UTR | TCG GAG CCG TGC CCA GCC TG | 88 | 118 |
| 9026 | 3'UTR | CGG GCC AGG TGT GAG GGA CT | 40 | 119 |
| 9027 | 3'UTR | CCG CGA CGC AGG CAC AGC AG | 40 | 120 |
| 9029 | 3'UTR | GGT CAG TGC ATC GAG TTC TG | 77 | 121 |

Oligonucleotides ISIS 9007, 9008, 9012, 9013, 9017, 9021, 9022, 9023, 9025 and 9029 gave greater than 50% inhibition of PKC-ζ mRNA expression in this assay and are preferred. Of these, ISIS 9022, ISIS 9023 and ISIS 9025 gave at least 85% inhibition and are more preferred.

Example 18

Effect of ISIS 3521 on the Growth of Human T24 Bladder Tumors in Nude Mice:

Subcutaneous human T24 bladder carcinoma xenografts in nude mice were established by injection of $5\times10^6$ T24 cells under the skin. Mice were treated with ISIS 3521 or ISIS 4559, a phosphorothioate scrambled version of the ISIS 3521 sequence, or ISIS 1082, an unrelated control phosphorothioate oligonucleotide targeted to Herpes simplex virus (oligonucleotide doses 0.006 mg/kg, 0.06 mg/kg, 0.6 mg/kg or 6.0 mg/kg) or saline administered intraperitoneally three times weekly. By day 21, ISIS 1082 or ISIS 4559 had no effect on tumor growth at any dose. By day 21, ISIS 3521 showed a dose-dependent inhibition of tumor growth at all dose levels, with a maximal inhibition of 90% at the 6 mg/kg dose.

Example 19

Effect of ISIS 3521 on the Growth of Human Colo-205 Colon Tumors in Nude Mice:

Subcutaneous human Colo-205 colon carcinoma xenografts in nude mice were established by injection of $5\times10^6$ Colo-205 cells under the skin. Mice were treated with ISIS 3521 and an unrelated control phosphorothioate oligonucleotide (ISIS 1082) administered intravenously once per day at a dosage of 6.0 mg/kg. In this study, ISIS 3521 inhibited tumor growth after 25 days by 84% compared to saline controls. The control oligonucleotide, ISIS 1082, inhibited tumor growth by 20%.

Example 20

Figure 13:
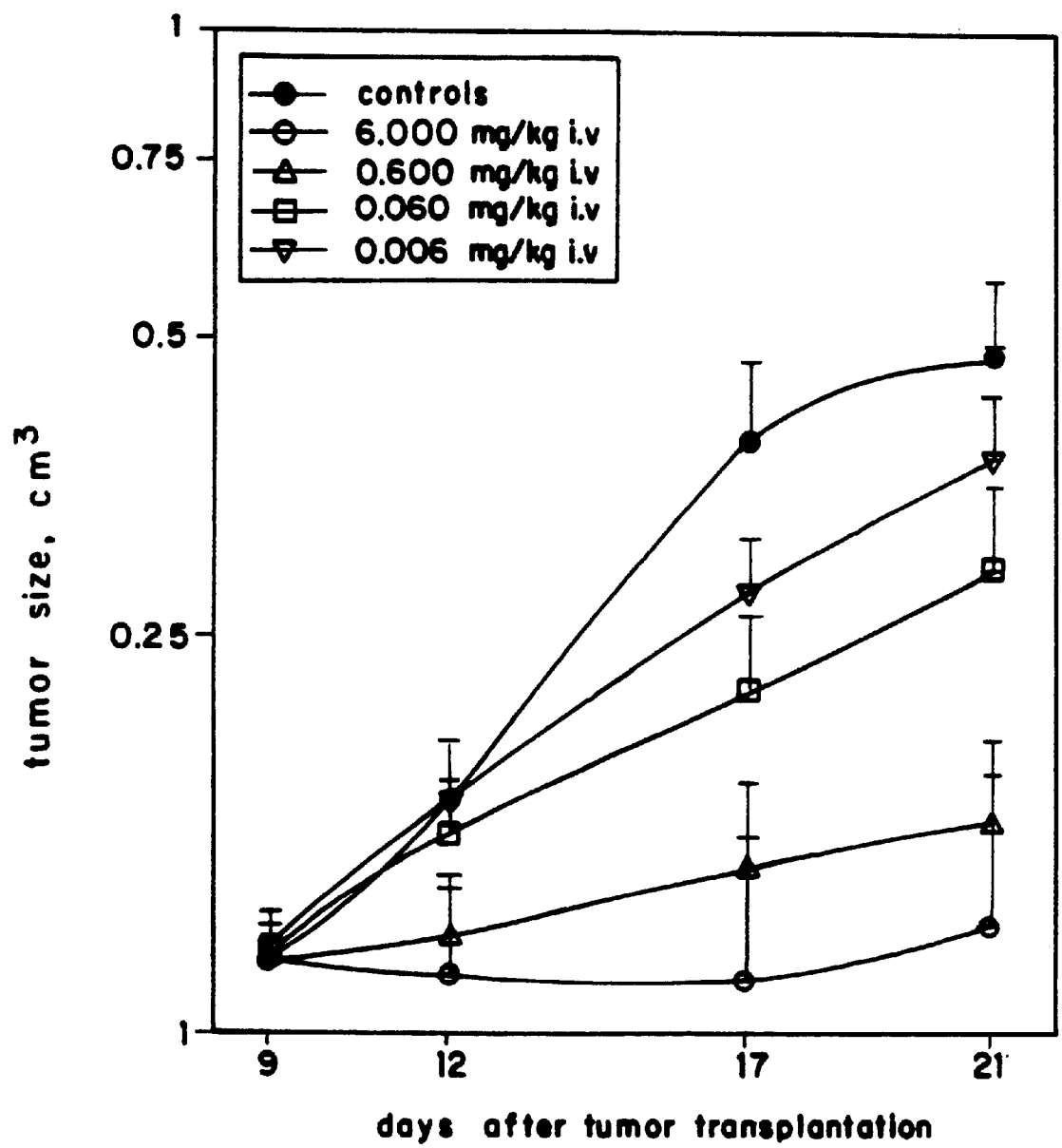
FIG. 13 is a line graph showing the effect of ISIS 8459 (2' fluoro gapped version of ISIS 3521) on the growth of A549 xenografts in nude mice. All doses (0.006, 0.06, 0.6. 6.0 mg/kg) of ISIS 8459 inhibit tumor growth.

Effect of ISIS 8469, a 2'-Fluoro Gapped Version of ISIS 3521, on the Growth of A549 Human Lung Tumors in Nude Mice:

Subcutaneous human A549 lung adenocarcinoma xenografts were established by injection of $5\times10^6$ A549 cells under the skin of Balb/c nude mice. Mice were treated with ISIS 8469, a chimeric version of ISIS 3521 having an 8-nucleotide deoxy gap flanked by six 2'-fluoro nucleotides on each side, as in Example 10. Oligonucleotide doses were from 0.006 mg/kg to 6.0 mg/kg. ISIS 8469 decreased tumor size at all doses in a dose-dependent manner, as shown in FIG. 13. This compound is therefore preferred.

Example 21

U-87 Human Glioblastoma Cell Culture and Subcutaneous Xenografts into Nude Mice:

The U-87 human glioblastoma cell line was obtained from the ATCC (Rockville Md.) and maintained in Iscove's DMEM medium supplemented with heat-inactivated 10% fetal calf serum. Nude mice were injected subcutaneously with $2\times10^7$ cells. Mice were injected intraperitoneally with ISIS 3521 at dosages of either 2 mg/kg or 20 mg/kg for 21 consecutive days beginning 7 days after xenografts were implanted. Tumor volumes were measured on days 14, 21, 24, 31 and 35. On day 35 (7 days after end of treatment), ISIS 3521 at 2 mg/kg had reduced tumor volume by 84% compared to saline or sense oligonucleotide control. The 20 mg/kg dose reduced tumor size by 91% on day 35.

Example 22

Effect of ISIS 3521 on PKC-α Protein Levels in U-87 Glioblastoma Xenografts in Nude Mice:

PKCα protein levels in subcutaneous U-87 tumor xenografts were measured by western blot analysis on day 24 (day 17 of treatment with ISIS 3521) and day 35 (7 days after end of treatment with ISIS 3521). An affinity-purified PKCα-specific polyclonal antibody (Life Technologies, Inc.) was used as the primary antibody. By day 24, ISIS 3521 was found to virtually totally abolish PKCα in the tumors. By seven days after cessation of oligonucleotide treatment (day 35), PKCα had returned to control levels.

Example 23

"Crossover Experiment" to Evaluate Effect of Switching Treatment on Tumor Size:

The two groups of mice with subcutaneous U-87 xenografts previously treated with ISIS 3521 (2 mg/kg or 20 mg/kg) were switched to different treatments on day 35 (7 days after the initial 21 day treatment had ended). The group which had previously received 20 mg/kg ISIS 3521 now received saline ("high dose-to-control"). The group which had received 2 mg/kg ISIS 3521 now received 20 mg/kg ISIS 3521 ("low dose-to-high dose"). This crossover treatment was continued for 21 days as for the original treatment.

Figure 14:
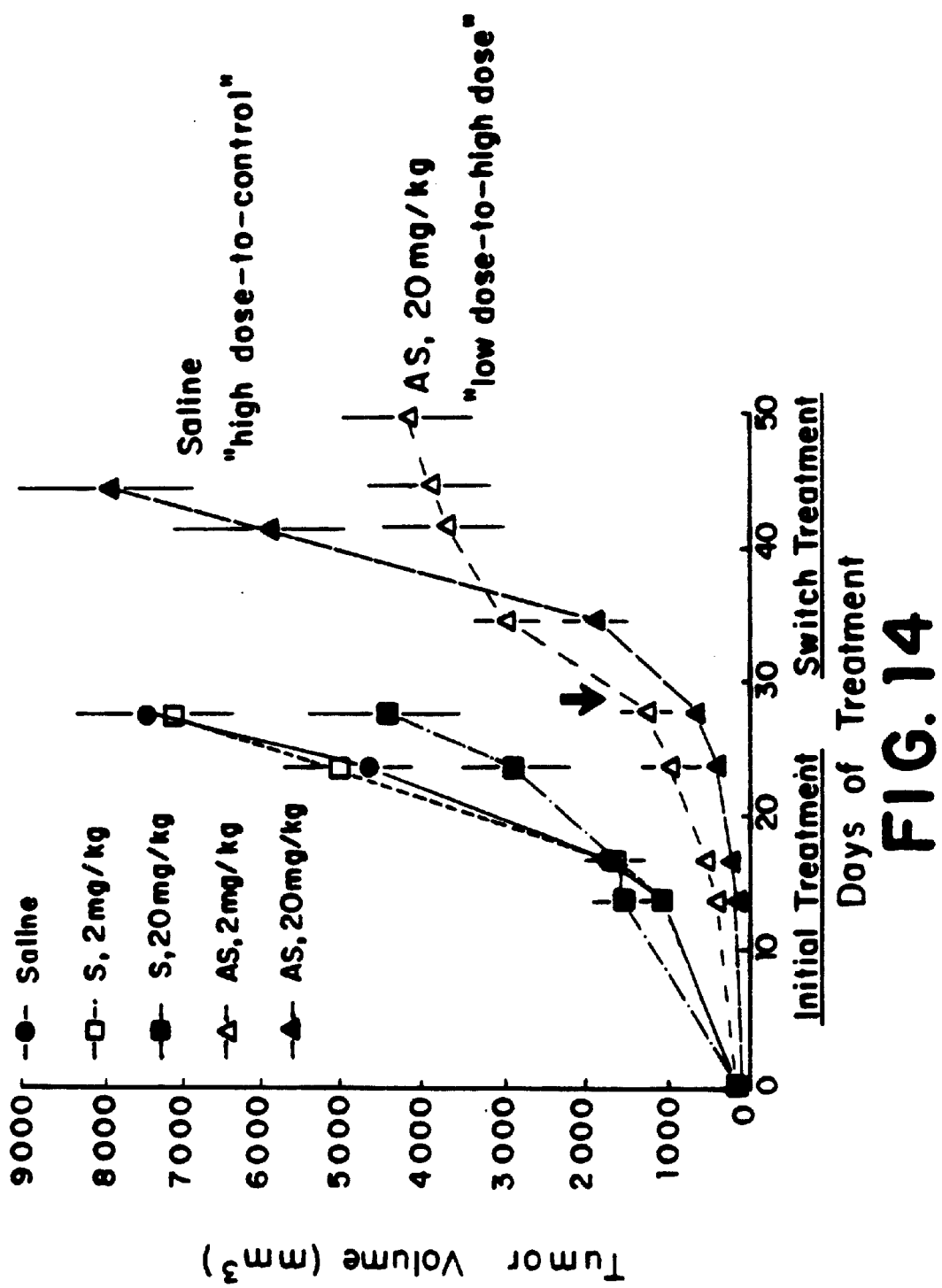
FIG. 14 is a line graph showing a "crossover" experiment to evaluate the effect of ISIS 3521 on U-87 glioblastoma cells in nude mice. The experiment was carried out with oligonucleotide doses of 2 mg/kg and 20 mg/kg and then treatment was switched (arrow). The group which had originally received ISIS 3521 at 20 mg/kg ("high dose-to-control" group, closed triangles) then received saline and the group which had originally received ISIS 3521 at 2 mg/kg ("low dose-to-high dose", open triangles) then received ISIS 3521 at 20 mg/kg. S=sense oligonucleotide (control); AS=antisense oligonucleotide (ISIS 3521) targeted to PKC-α.

As shown in FIG. 14, the growth of the tumors in the "low dose-to-high dose" group (open triangles) leveled off after treatment was switched (arrow). The growth of the tumors in the "high dose-to-control" group (closed triangles) rapidly accelerated after switching to saline treatment (arrow). S=sense oligonucleotide (control); AS=antisense oligonucleotide (ISIS 3521) targeted to PKCα.

Example 24
Effect of ISIS 3521 on Intracerebral U-87 Glioblastoma Xenografts into Nude Mice:

U-87 cells how were implanted in the brains of nude mice. Mice were treated via continuous intraperitoneal administration of antisense oligonucleotide ISIS 3521 (20 mg/kg), control sense oligonucleotide (20 mg/kg) or saline beginning on day 7 after xenograft implantation. All mice survived until day 25, at which point the saline-treated mice began to die. All saline-treated mice and sense oligonucleotide-treated mice were dead by day 41. In contrast, all ISIS 3521-treated mice were alive until approximately day 37, and half of the mice were still alive at day 61. At the termination of the experiment at day 80, 40% of the ISIS 3521-treated mice were still alive.

Example 25
Phase I/II Trial of ISIS 3521 with Carboplatin and Paclitaxel in NSCLC:

An initial phase I escalating dose study was performed on patients with multiple tumor types, and safety and pharmacokinetic evaluations were performed. Activity in 12 NSCLC patients led to expansion of the study at additional centers where response rate, time to progression and survival were determined. The ISIS 3521 plus carboplatin/paclitaxel study had the following inclusion criteria: age at least 18, ECOG<2, measurable or evaluable disease, no prior chemotherapy, no central nervous system metastases, and adequate hematologic, renal and hepatic function. The dosing schedule was day 0–14: ISIS 3521 2.0 mg/kg/day by continuous intravenous infusion (24 hrs); day 3: paclitaxel 175 mg/m$^2$ (3 hrs), carboplatin AUC 6 (1 hr); and day 15–21: 7 day rest period. Tumor re-staging was performed every 2 cycles. Treatment was continued for 6 cycles if no disease progression present. Fifty-three patients were enrolled in the study. The median age was 60 (range= 32–79), with 34 males and 19 females. The performance status ECOG 0:1 was 25:28. The histology was adenocarcinoma 38, squamous cell 7 and large cell/other 8. The disease stage was 9 stage IIB and 44 stage IV. The metastatic sites were lung (35), nodes (16), liver (10), adrenal (6) and bone (5). Thirty-eight patients had 1–2 sites, and 6 patients had >2 sites. The total number of dosing cycles was 258 with a median of 6 (range 1–9). Dose reductions were carboplatin 6pts, paclitaxel 2 pts and ISIS 3521 2 pts. In 19 patients, cycles were delayed greater than one week (13 pts), and hematologic recovery was observed in 12 patients (6 pts). Non-hematologic comp. was observed in two patients, central line comp. In two patients and patient request in three patients.

Figure 15:
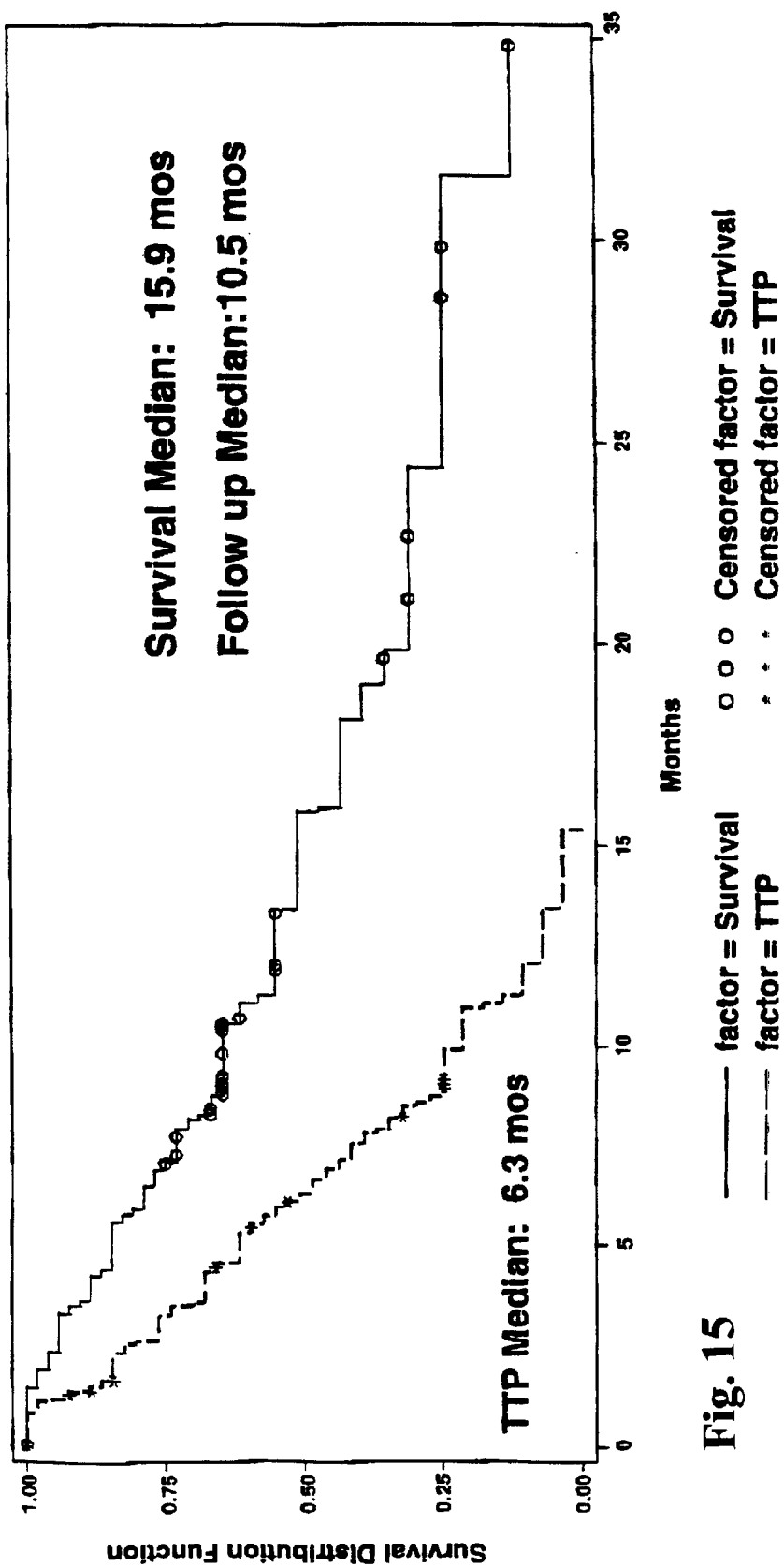
FIG. 15 is a graph showing the time to progression and overall survival in a phase I/II human clinical cancer study with ISIS 3521 combined with carboplatin and paclitaxel.

Grade 3 adverse effects were neutropenia (26%), thrombocytopenia (21%), infection (17%), asthenia (8%), fever (8%), neutropenic fever (8%) and thrombosis (8%). Grade 4 adverse effects were neutropenia (43%), thrombocytopenia (11%) and infection (2%), but no episodes of grade 3 or 4 neuropathy. Out of the 53 patients enrolled, five were not evaluable for response due to pneumonia (1), thrombosis (1), paclitaxel reaction (2) and non-compliance (1). Thus, 48 patients were evaluable for response. The responses were as follows: complete (1), partial (21), minor (5), stable disease (12) and progressive disease (9), with an overall response rate of 46%. The time to progression and overall survival is shown in FIG. 15. At a median follow up of 13 months, the median overall survival is 15.9 months with an actuarial 1-year survival of 56%; the median time to progression is 6.7 months.

Example 26
Phase I/II Trial of ISIS 3521 with Cisplatin and Gemcitabine in Advanced Non-small Cell Lung Cancer (NSCLC):

This phase I/II trial initially evaluated the safety of ISIS 3521 2 mg/kg/day, administered by continuous IV infusion days 0–14 plus cisplatin 80 mg/m$^2$ day 0 and gemcitabine 1,000 mg/m$^2$ days 0 and 7. The combination was well tolerated, with grade 3–4 neutropenia and thrombocytopenia in 57% and 43% of cycles, respectively, in 7 patients with advanced cancer. No pharmacokinetic interactions were observed. In the phase II portion, data are available for 43 of 44 advanced, previously-untreated NSCLC patients (24 F, 19 M). Patients: median age, 64.5 (range 38–85); PS, 0/1 (43%/57%); stage IV disease, 40 patients (93%). With 12 patients still on treatment, a median of 3 cycles have been administered (range 1–7). Toxicity: thrombocytopenia (grade 3: 23 patients; grade 4: 15 patients), neutropenia (grade 3: 6 patients; grade 4: 13 patients), anemia (grade 3: 6 patients), fatigue (grade 3: 11 patients), dehydration (grade 3: 6 patients; grade 4: 1 patient), sepsis (grade 3: 2 patients; grade 4: 1 patient, none with neutropenia), neutropenic fever (2 patients). There was no grade 3/4 neuropathy or azotemia. Thirty-one patients are evaluable for response: 1 CR (3%), 11 PR (35%), 17 SD (55%), 2 PD (7%). ISIS 3521 combined with cisplatin and gemcitabine is well tolerated and shows promising efficacy in advanced NSCLC.

Example 27
Phase II Trial of ISIS 3521 with Docetaxel in Non-small Cell Lung Cancer (NSCLC):

This phase II study examined the safety and efficacy of ISIS 3521 combined with docetaxel in patients with stage IIIB/IV, previously-treated NSCLC. Dosing and safety data are available for 53 of 57 patients enrolled. Thus far, patients (31 M, 22F) have received a median of 2 (range 1–8) cycles of ISIS 3521 (2 mg/kg/day by fixed daily dose) by continuous IV infusion on days 0–14 plus docetaxel 75 mg/m$^2$ on day 3. Treatment is ongoing in 10 patients. Median age: 58 (range 29–78); stage IV disease: 87%. Performance status was 0/1/2 in 44%/42%/14%. Grade 3/4 hematologic toxicities: neutropenia (grade 3: 5 patients; grade 4: 6 patients), thrombocytopenia (grade 3: 9 patients; grade 4: 0 patients). Most common other adverse effects: fatigue (grade 3: 4 patients; grade 4: 1 patient). There was no episodes of grade 3 of 4 neuropathy. Response data are available for 36 patients. Best responses to date: partial response, 5 patients (14%, two of whom failed prior paclitaxel); stable disease, 15 patients (42%); progressive disease, 16 patients (44%). ISIS 3521 combined with docetaxel is well tolerated, without evidence of unusual toxicity and shows evidence of anti-tumor activity.

Example 28
Clinical and Pharmacokinetic Study of ISIS 3521 Administered in Combination with 5-Fluorouracil and Leucovorin in Patients with Advanced Cancer:

Patients with refractory solid tumors received ISIS 3521 as a 21-day continuous infusion administered simultaneously with 5-fluorouracil (425 mg/m$^2$/day) and leucovorin (20 mg/m$^2$/day) daily for 5 consecutive days repeated every 4–5 weeks (one cycle). Pharmacokinetic analysis was performed on samples taken during the first cycle in all patients and samples were assayed for full-length oligonucleotide and chain-shortened metabolite concentrations by capillary gel electrophoresis. 5-fluorouracil concentrations were assayed in plasma by high performance liquid chromatography (HPLC).

Fifteen patients received ISIS 3521 at one of three dose levels: 1.0 (n=3 pts), 1.5 (n=3 pts) and 2.0 (n=9 pts) mg/kg/day. All patients simultaneously received 5-fluorouracil and leucovorin. Grade 1–2 toxicities included alopecia, fatigue, mucositis, diarrhea, anorexia, nausea/vomiting and tumor pain. One patient had grade 3 chest pain considered related to 5-fluorouracil therapy; another patient had dose-limiting grade 3 mucositis resolving in less than 7 days; and one patient with a history of gastritis had an acute upper gastrointestinal bleed thought to be 5-fluorouracil induced toxicity. Five patients developed cycle 1 grade 4 neutropenia, which resolved without colony stimulating factors before the next treatment cycle. There were no effects on prothrombin time and activated partial thromboplastin time. A clinically defined MTD was not reached. The mean steady-state levels (CsK) levels for ISIS 3521 increased with dose with >60% of the oligonucleotide remaining intact (parent sequence) at the end of sampling. ISIS 3521 pharmacokinetics in the presence of 5-fluorouracil were consistent with those reported previously. 5-fluorouracil pharmacokinetic parameters were also similar in the presence or absence of ISIS 3521. Six of 14 patients (about 43%) across all dose cohorts had an improvement in measurable tumor response ranging from minor reduction in tumor size (4 patients) to objective partial response (>50% reduction in tumor size, 2 patients).

ISIS 3521 is tolerable at its recommended single agent dose when given with 5-fluorouracil and leucovorin. Antitumor activity was observed with the combinations.

Example 29

Safety and Efficacy Trial of ISIS 3521 in Patients with Low-grade, Non-Hodgkin's Lymphoma:

In a Phase 1 trial of ISIS 3521, two complete responses were observed in patients with heavily pretreated, indolent non-Hodgkin's lymphoma (NHL). In this phase II, multicenter trial, 29 patients with advanced relapsed or refractory low-grade or follicular NHL received ISIS 3521, 2 mg/kg/day, by 21-day continuous IV infusion repeated every 4 weeks. To date, 26 are evaluable for toxicity and 21 for efficacy. Patients: male 15, female 11; median age 62 years (range 29–86); histology, follicular 16 (small cleaved 9, mixed 5, large cell 2), SLL 10; tumor stage III-IV, 22; PS 0/1/2, 14/6/5 (1 NA); median # of prior treatments 3 (range 1–10). To date, 51 cycles have been administered (median 2, range 1–6) Eight patients continue on treatment. Grade 3–4 thrombocytopenia occurred in 7 patients (6 grade 3, 1 grade 4), requiring dose reduction in two. Two patients had grade 3 fatigue, requiring dose reduction in one. One patients had dose reduction with signs of acute tumor lysis (hyperuricemia, reduced lymphocytosis, painful nodal/splenic sites). Another developed a picture of self-limited toxic hepatitis concurrent with allopurinol therapy to prevent acute tumor lysis. One patient had a mixed response. This patient had a 73% reduction in measurable disease, received radiation to three subcutaneous nodules, and continues with an excellent response after 8 months of ongoing treatment. Other best responses: stable disease (16 patients), progressive disease (4 patients). Median time to progression is currently 2.1 months (95% CI, 1.9–7.3 months), with follow-up ongoing. ISIS-3521 antisense oligonucleotide treatment is well tolerated in patients with NHL. The observed modest activity is comparable to that observed with other oligonucleotides in NHL.

What is claimed is:

1. A pharmaceutical composition comprising an oligonucleotide up to 50 nucleotide units in length comprising SEQ ID NO: 2, in combination with carboplatin and paclitaxel.

2. The pharmaceutical composition of claim 1, wherein said oligonucleotide comprises at least one phosphorothioate linkage.

3. The pharmaceutical composition of claim 1, wherein said oligonucleotide has the sequence shown in SEQ ID NO: 2.

4. A pharmaceutical composition comprising an oligonucleotide up to 50 nucleotide units in length comprising SEQ ID NO: 2, in combination with docetaxel.

5. The pharmaceutical composition of claim 4, wherein said oligonucleotide comprises at least one phosphorothioate linkage.

6. The pharmaceutical composition of claim 4, wherein said oligonucleotide has the sequence shown in SEQ ID NO: 2.

7. A pharmaceutical composition comprising an oligonucleotide up to 50 nucleotide units in length comprising SEQ ID NO: 2, in combination with cisplatin and gemcitabine.

8. The pharmaceutical composition of claim 7, wherein said oligonucleotide comprises at least one phosphorothioate linkage.

9. The pharmaceutical composition of claim 7, wherein said oligonucleotide has the sequence shown in SEQ ID NO: 2.

10. A pharmaceutical composition comprising an oligonucleotide up to 50 nucleotide units in length comprising SEQ ID NO: 2, in combination with 5-fluorouracil and leucovorin.

11. The pharmaceutical composition of claim 10, wherein sad oligonucleotide comprises at least one phosphorothioate linkage.

12. The pharmaceutical composition of claim 10, wherein said oligonucleotide has the sequence shown in SEQ ID NO: 2.

13. A method of inhibiting PKC-α expression in human cells comprising contacting the cells with the pharmaceutical composition of claims 1, 4, 7 or 10.

14. The method of claim 13 wherein the cells are cancer cells.

15. A method of treating a condition associated with expression of human PKC-α comprising administering to an animal or cells, tissues or a bodily fluid thereof, a therapeutically effective amount of the pharmaceutical composition of claims 1, 4, 7 or 10.

16. The method of claim 15 wherein said condition is cancer.

17. A method of treating non small cell lung cancer (NSCLC) in a human in need thereof, comprising administering to said human the pharmaceutical composition of claim 1.

18. A method of treating non-Hodgkin's lymphoma in a human in need thereof, comprising administering to said human a pharmaceutical composition comprising an oligonucleotide up to 50 nucleotide units in length comprising SEQ ID NO: 2.

* * * * *

UNITED STATES PATENT AND TRADEMARK OFFICE
CERTIFICATE OF CORRECTION

PATENT NO.     : 6,537,973 B1
DATED          : March 25, 2003
INVENTOR(S)    : Frank C. Bennett It is certified that error appears in the above-identified patent and that said Letters Patent is hereby corrected as shown below:

<u>Title page,</u>
Item [56], References Cited, OTHER PUBLICATIONS,
"Stec, et al.," reference, please delete "sterocontrolled" and insert therefor
-- Stereocontrolled --; and please delete (in both occurrences) "Phosphorothiates" and insert therefor -- Phosphorothioates--;
"Holy A.," reference, please delete "5`-methanephosponate" and insert therefor
-- 5`-methanephosphonate --;
"Wijnen, M.H.," reference, please delete "Wijen" and insert therefor -- Wijnen --;
"Marcus-Sekura, C.J., et al.," reference, please delete "Linkates" and insert therefor
-- Linkages --;
"Rayne, R.C., and O'Shea, M.," reference, please delete "instect" and insert therefor
-- Insect --;
"Farese, et al.," reference, please delete "(beat and alpha)" and insert therefor (Beta and Alpha) --;
"Maier, et al.," reference, please delete "Humna" and insert therefor-- Human --;
"Ikehara, et al.," 5th reference, please delete "Deoxyandenylic" and insert therefor
-- Deoxyadenylic --;
"Ikehara, et al.," 5th reference, please delete "Deoxyandenylic" and insert therefor
-- Deoxyadenylic --;
"Walder, R.Y. and Walder, J.A.," reference, please delete "Hydbrid-Arested" and insert therefor -- Hybrid-Arrested --;
"Ikehara, M. and Imura, J.," reference, please delete "fo" and insert therefor -- Of --;

Signed and Sealed this

First Day of June, 2004

JON W. DUDAS
*Acting Director of the United States Patent and Trademark Office*